(12) United States Patent
Baek et al.

(10) Patent No.: US 8,927,220 B2
(45) Date of Patent: Jan. 6, 2015

(54) METHOD FOR DIAGNOSING IMMUNOGLOBULIN A NEPHROPATHY AND TGBM NEPHROPATHY

(75) Inventors: Moon Chang Baek, Daegu (KR); Pyong Gon Moon, Jinju KyungNam (KR); Yong Lim Kim, Daegu (KR)

(73) Assignee: Kyungpook National University Industry-Academic Cooperation Foundation, Daegu (KR)

( * ) Notice: Subject to any disclaimer, the term of this patent is extended or adjusted under 35 U.S.C. 154(b) by 530 days.

(21) Appl. No.: 13/002,224

(22) PCT Filed: Sep. 30, 2009

(86) PCT No.: PCT/KR2009/005589
§ 371 (c)(1),
(2), (4) Date: Jun. 7, 2011

(87) PCT Pub. No.: WO2010/038974
PCT Pub. Date: Apr. 8, 2010

(65) Prior Publication Data
US 2011/0236913 A1    Sep. 29, 2011

(30) Foreign Application Priority Data
Oct. 1, 2008 (KR) .................. 10-2008-0096862

(51) Int. Cl.
| | | |
|---|---|---|
| *G01N 33/573* | (2006.01) | |
| *G01N 33/68* | (2006.01) | |
| *G01N 33/564* | (2006.01) | |
| *C07K 16/38* | (2006.01) | |
| *C07K 16/40* | (2006.01) | |
| *G01N 33/543* | (2006.01) | |
| *G01N 1/40* | (2006.01) | |

(52) U.S. Cl.
CPC ...... *G01N 33/6893* (2013.01); *G01N 2800/347* (2013.01); *G01N 2333/8125* (2013.01); *G01N 33/6842* (2013.01); *G01N 2333/90287* (2013.01); *G01N 33/5436* (2013.01); *G01N 33/573* (2013.01); *G01N 2333/79* (2013.01); *G01N 2001/4083* (2013.01); *G01N 2800/7095* (2013.01); *G01N 2333/4713* (2013.01); *C07K 16/38* (2013.01); *G01N 33/564* (2013.01); *C07K 16/40* (2013.01); *G01N 2800/24* (2013.01); *Y10S 435/973* (2013.01); *Y10S 436/811* (2013.01); *Y10S 530/811* (2013.01)
USPC ............. 435/7.1; 435/7.4; 435/15; 435/23; 435/973; 436/501; 436/518; 436/86; 436/811; 530/388.25; 530/388.26; 530/389.3; 530/391.1; 530/811

(58) Field of Classification Search
CPC ........ C07K 16/38; C07K 16/40; G01N 33/53; G01N 33/536; G01N 33/537; G01N 33/543; G01N 33/5436; G01N 33/554; G01N 33/564; G01N 33/573; G01N 2001/4083; G01N 2333/435; G01N 2333/4713; G01N 2333/79; G01N 2333/81; G01N 2333/8125; G01N 2333/90287; G01N 2570/00; G01N 2800/24; G01N 2800/347; G01N 2800/50; G01N 2800/7095; G01N 33/6842; G01N 33/6893; Y10S 435/973; Y10S 436/811
USPC ......... 435/7.1, 7.4, 15, 23, 287.2, 287.9, 973, 435/975; 436/501, 518, 15, 16, 86, 811, 436/824; 530/380, 388.25, 388.26, 389.3, 530/391.1, 413, 811, 812
See application file for complete search history.

(56) References Cited

U.S. PATENT DOCUMENTS

| | | | | |
|---|---|---|---|---|
| 7,838,634 | B2 * | 11/2010 | Haab et al. ................ | 530/387.1 |
| 7,897,356 | B2 * | 3/2011 | Klass et al. .................. | 435/7.1 |
| 8,354,234 | B2 * | 1/2013 | Chen et al. ................... | 435/7.1 |
| 2007/0178538 | A1 * | 8/2007 | Haab ........................... | 435/7.23 |

FOREIGN PATENT DOCUMENTS

WO    2007/082586 A1 *  7/2007

OTHER PUBLICATIONS

Rao et al., 2007. Proteomic identification of urinary biomarkers of diabetic nephropathy. Diabetes Care 30: 629-637.*
Park et al., 2006. Establishment of a 2-D human urinary proteomic map in IgA nephropathy. Proteomics 6: 1066-1076.*
Norden et al., 2001. Glomerular protein sieving and implications for renal failure in Fanconi syndrome. Kidney International 60: 1885-1892.*

* cited by examiner

*Primary Examiner* — Gail R Gabel
*Assistant Examiner* — James L Grun
(74) *Attorney, Agent, or Firm* — Rothwell, Figg, Ernst & Manbeck, P.C.

(57) ABSTRACT

A protein used as a biomarker for diagnosing IgA nephropathy and TGBM (thin-glomerular-basement-membrane) using urine through a target proteomics method. A diagnosis biomarker protein and a kit for diagnosing IgA nephropathy and TGBM and predicting progress of the nephropathy in advance using the protein are provided. The degree of the progression of the disease can be grasped by detecting IgA nephropathy and TGBM, enabling early diagnosis and confirming progress from the patient's urine. In addition, a monoclonal antibody produced based on the diagnosis biomarker protein can be used for an immunoassay kit (ELISA, antibody coated tube test, lateral-flow test, potable biosensor). The monoclonal antibody is used in early diagnosis and progression detection of IgA nephropathy and development of a novel drug for the purpose of treatment.

2 Claims, 2 Drawing Sheets

METHOD FOR DIAGNOSING IMMUNOGLOBULIN A NEPHROPATHY AND TGBM NEPHROPATHY

CROSS REFERENCE TO RELATED APPLICATION

This application is a 35 U.S.C. 371 National Phase Entry Application from PCT/KR2009/005589, filed Sep. 30, 2009, which claims the benefit of Korean Patent Application No. 10-2008-0096862 filed on Oct. 1, 2008, the disclosure of which is incorporated herein in its entirety by reference.

TECHNICAL FIELD

The present invention relates to development of a protein that can be used for diagnosing IgA nephropathy and thin-glomerular-basement-membrane (hereinafter, referred to as "TGBM") nephropathy, and used as a biomarker for diagnosing serious cases thereof, and more particularly to a biomarker protein that shows increased/decreased levels in urine of IgA nephropathy patients or TGBM nephropathy patients compared to those in urine of normal people, and a diagnostic kit using the biomarker protein, which can be used to diagnose IgA nephropathy and TGBM nephropathy early, and predict and determine the degree of progression of the disease in advance.

BACKGROUND ART

IgA nephropathy is one of the various diagnoses of glomerulonephritis, and is known to be the most frequent glomerulonephritis in foreign countries as well as Korea. Its cause is not well known. When bacteria invade a body, an immunity substance referred to as an "antibody" is required to struggle against the bacteria. However, a phenomenon in which immunoglobulin A (IgA), one of such antibodies, reaches a kidney's glomerulus and destroys it without struggling against bacteria is referred to as IgA nephropathy. At present, the representative biomarkers for determining the degree of progression of IgA nephropathy include proteinuria and creatine. However, proteinuria is highly related to a marker for other diseases in that it is also a marker indicating occurrence of hypertension and cardiovascular diseases as well as IgA nephropathy, and thus it is difficult to directly determine the degree of progression of diabetic nephropathy. Also, TGBM nephropathy causes symptoms such as haematuria and proteinuria. Although such symptoms are similar to those of IgA nephropathy, TGBM nephropathy is a disease with a relatively favorable prognosis. However, it is impossible to accurately diagnose IgA nephropathy by only such a history (including a cause, symptoms, and progress with the passage of time, etc. of a patient's disease), and a kidney biopsy is required for accurate diagnosis.

Accordingly, when a novel diagnosis marker having clinically high specificity and sensitivity, and a monoclonal antibody for detecting the marker are developed, it is possible to develop a kit which can diagnose diabetic nephropathy early and the degree of progression can be predicted in advance.

Accordingly, the present inventors attempted to conduct research for overcoming problems of the above described conventional technologies. As a result, they have completed the present invention by identifying biomarkers of diseases such as IgA nephropathy and TGBM nephropathy through a target proteomics technique.

IgA nephropathy is the most frequent glomerulonephritis in Korea. It may occur in all age groups, but mainly occurs in people in their teens and twenties. Its clinical features are various. Intermittent visible haematuria may occur accompanied by upper respiratory tract infection, or persistent microscopic haematuria and proteinuria occur. In some cases, IgA nephropathy is expressed as nephritic syndrome, acute nephritis, or hypertension. Also, in many cases, IgA nephropathy progresses while being unknown to patients, and then is found as chronic renal failure. It has been reported that IgA nephropathy is slowly progresses, and finally progresses to a terminal kidney disease in about 30% or more of patients within 20 years. However, IgA nephropathy shows various clinical progresses. Known risk factors that have an effect on prognosis include persistent proteinuria, depression in renal function, persistent hypertension, old age, being male, and histological findings, etc. IgA nephropathy is a kind of immune complex-mediated glomerular disease. Its basic cause is a control disorder of an immune reaction against an antigen coming into a mucous membrane, etc., by which polymeric IgA1 is excessively produced in bone marrow, and at the same time the structure deficiency of IgA1 occurs. As a result, polymeric IgA1 is deposited in mesangium, and damage is caused by mediators. Optical microscopic findings on IgA nephropathy characteristically include focal or diffuse cell proliferation, and expansion of extracellular matrix in mesangium. The cell proliferation occurs in various ways and even causes crescent formation. Vascular lesion and tubulointerstitial lesion are also observed. Immunofluorescence is necessary for a diagnosis of IgA nephropathy because it shows that IgA is significantly deposited in mesangium. In general, IgA is deposited together with C3, IgG, IgM, etc. Electron microscopic findings are characterized in that high electron dense deposits are observed in mesangium or its periphery, and subendothelial deposits are locally observed in the periphery of the mesangium.

There are patent disclosures concerning research on a diagnosis method of IgA nephropathy. Korean laid-open patent No. 1999-82292 discloses a method of obtaining a novel gene from an IgA renopathy patient's leukocytes by using a differential•display method, an IgA nephropathy diagnostic agent including oligonucleotide derived from a leukocyte, and a therapeutic agent. Korean registered patent No. 528664 discloses an IgA protein for diagnosing diabetic retinopathy, a diagnostic kit including an IgA protein antibody, and a diagnosis method. Korean laid-open patent No. 2004-54609 discloses a method for relating a gene expression profile to a protein expression profile in identifying a target protein related to a disease such as an autoimmune disease to identify new drug development and a diagnosis marker. US patent publication No. 2007/87448 discloses a general method for diagnosing the progress stage of a disease by collecting a physiological specimen from blood and urine of a subject, obtaining a spectroscopic peak through the mass spectrometry of the specimen, and using protein profile analysis information obtained from the peak. Korean registered patent No. 792630 discloses a method for early diagnosis and progress stage determination of diabetic nephropathy in diabetes mellitus, in which the occurrence, early diagnosis, progress stage, and symptom severity of diabetic nephropathy in diabetes mellitus are determined from blood of a person, and a monoclonal antibody prepared based on an identified protein is used for an immunoassay kit.

Although it is important to diagnose early and treat IgA nephropathy or TGBM nephropathy before serious depression in renal function occurs in IgA nephropathy patients or TGBM nephropathy patients, it is difficult to determine whether to carry out an invasive test such as renal biopsy in young adults showing only hematuria or proteinuria without symptoms in order to diagnose the nephropathy. Furthermore, in a case of renal biopsy, it is difficult to actually carry out the biopsy in all patients for various reasons. Therefore, there is a need to develop a novel method or kit for diagnosing IgA nephropathy or TGBM nephropathy, which is simple and accurate.

DISCLOSURE

Technical Problem

Therefore, the present invention has been made in view of the above-mentioned problems and requirements, and a principle object of the present invention is to provide a novel biomarker protein or an immunogenic fragment thereof, which can be used to diagnose IgA nephropathy and TGBM nephropathy early, and their degrees of progression can be effectively detected.

Another object of the present invention is to provide an antibody against the biomarker protein, and a composition and a diagnostic kit which use the same.

Technical Solution

In accordance with an aspect of the present invention, a biomarker for diagnosing IgA nephropathy and TGBM nephropathy, which includes, as an active component, proteins selected from the group including proteins increased/decreased levels in urine of nephropathy subjects compared to those levels in urine of normal people is provided. In order to obtain a diagnosis biomarker protein, label-free quantification was used. For convenience of analysis and reproducibility, all nephropathy patient groups subjected to tests in the Examples, i.e., both the group of IgA nephropathy patients (hereinafter, referred to as a "IgAN group"), and the group of TGBM patients (hereinafter, referred to as a "TGBM group") were limited to only teenagers. Also, instead of all proteins in patients' urine, only exosomes within the urine were separated and used for the tests in the Examples.

In the present invention, a subject means an IgA nephropathy patient or a TGBM nephropathy patient, and an immunogenic fragment means a fragment of biomarker protein which has at least one epitope recognizable by the antibody against the biomarker protein of the present invention.

In another aspect of the present invention, the present invention provides a diagnostic agent for IgA nephropathy and/or TGBM nephropathy, which includes, as an active component, an antibody that is specifically bound to the biomarker protein of the present invention or the immunogenic fragment thereof. The antibody of the present invention may be a polyclonal antibody, but preferably a monoclonal antibody.

The polyclonal antibody may be produced by injecting a biomarker protein or a fragment thereof, as an immunogen, into a foreign host, according to a conventional method known to those skilled in the art. The foreign host includes mammals such as a mouse, a rat, a sheep, a rabbit, and the like. The immunogen is injected through intramuscular, intraperitoneal or subcutaneous injection, and is generally administered together with an adjuvant for improving antigenicity. From the foreign host, blood is periodically collected to collect blood serum showing improved titer and antigenic specificity, from which blood serum an antibody is separated and purified.

The monoclonal antibody may be produced by a technology for producing immortalized cell lines by fusion, known in the art [Koeher and Milstein 1975, Nature, 256:495)]. Hereinafter, the production method will be simply described. First, 20 μg of pure protein is obtained, and is immunized into a Balb/C rat. Otherwise, peptide is synthesized, bound to bovine serum albumin, and immunized into a rat. Then, antigen-producing lymphocyte separated from the rat is fused with myeloma of a human or a mouse to produce immortalized hybridoma. Then, ELISA method is used to select and proliferate only hybridoma cells producing a required monoclonal antibody, and the monoclonal antibody is separated and purified from that culture.

In order to accomplish a further object of the present invention, the present invention provides a method for diagnosing the degree of progression of diabetic nephropathy of a subject, the method including the step of detecting the biomarker protein or the immunogenic fragment thereof, according to the present invention, from a fluid of the subject. In the diagnosis method of the present invention, human blood is used. Also, in the detecting step, from a blood solution of the subject, the existence of the biomarker protein or the immunogenic fragment thereof are directly detected through two dimensional (2-D) electrophoresis. Otherwise, the blood can be contacted with the antibody of the present invention, to thereby indirectly detect the biomarker protein or the immunogenic fragment thereof through an antigen-antibody reaction.

Immunoassay methods, which are widely known to include antigen-antibody reactions, may include an enzyme immunoassay method (ELISA, Coated tube), a magnetic particle method (in which antibody-bound magnetic particles are bound to a tube, antigen-tracer and non-degradable pollutants are competitively reacted with each other to cause an enzyme reaction, and quantification is carried out), a latex particle method using antibody-bound latex particles, and the like. In another aspect of the present invention, the present invention provides a kit for diagnosing diabetic nephropathy, which includes, as an active component, an antibody specifically bound to the biomarker protein of the present invention or an immunogenic fragment thereof.

The diagnostic kit of the present invention is manufactured by a conventional manufacturing method known in the art, and typically includes freeze-dried antibody and buffer, stabilizer, inactive protein, and the like. The antibody may be labeled with a radioisotope, a fluorophore, an enzyme, or the like. The monoclonal antibody of the present invention may be variously used for an immunoassay kit (ELISA, antibody coated tube test, lateral-flow test, potable biosensor), and also may be used to develop a protein chip having a detection spectrum for various diabetic complications through development of an antibody showing higher specificity and sensitivity.

In accordance with another aspect of the present invention, the present invention provides a composition for treating and preventing IgA nephropathy or TGBM nephropathy, which includes, as an active component, protein selected from the group including proteins that show increased/decreased levels in urine of IgA nephropathy patients or TGBM nephropathy patients.

The pharmaceutical composition of the present invention may be prepared as a formulation such as a parenteral injection by mixing with a pharmaceutically acceptable carrier, an excipient, a diluent, etc. according to a method known in the pharmacological field, and then may be administered through intravenous injection, etc. The dose of the pharmaceutical composition according to the present invention may be appropriately selected depending on age, sex, severity, and disease symptoms of a patient, and preferably, 0.001 to 100 mg of protein per day per adult may be administered.

Advantageous Effects

The present invention can easily diagnose IgA nephropathy or TGBM nephropathy from urine. There has been no commercially available efficient diagnostic agent for diagnosing IgA nephropathy patients or TGBM nephropathy patients so far. The biomarker protein composition of the present invention is very advantageous in that it can simply diagnose IgA/TGBM nephropathy from urine of IgA nephropathy patients or TGBM nephropathy patients, and can diagnose diabetic nephropathy early and predict the degree of disease progression in advance.

Also, monoclonal antibodies prepared based on the biomarker proteins of the present invention can be used for an immunoassay kit (ELISA, antibody coated tube test, lateral-flow test, potable biosensor) capable of diagnosing IgA nephropathy and TGBM nephropathy early, and predicting the degree of disease progression. Furthermore, the antibody showing higher specificity and sensitivity can be used for developing a protein chip having a detection spectrum for early diagnosis and disease progression detection of IgA nephropathy and TGBM nephropathy from among various glomerular nephritis diseases.

BRIEF DESCRIPTION OF THE DRAWINGS

The foregoing and other objects, features and advantages of the present invention will become more apparent from the following detailed description when taken in conjunction with the accompanying drawings in which.

BEST MODE

Figure 1:
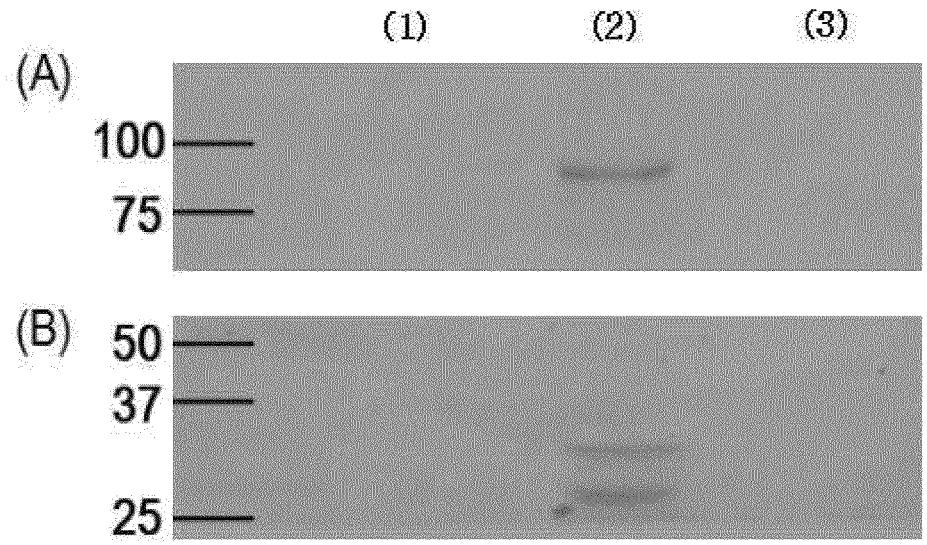
FIG. 1 shows electrophoresis photographs on the purity of separated exosomes, analyzed by western blot.

Hereinafter, the present invention will be described in detail with reference to Examples. These Examples are intended to only illustrate the present invention, and are not intended to limit the scope of the present invention.

Example 1

Urinary Sample Preparation

All urine samples of patients and normal people were provided from Kyung-pook National University Hospital. From among urine samples collected from July 2006 to April 2008, urine samples of 5 IgA nephropathy patients and 7 TGBM nephropathy patients, which were confirmed through renal biopsy of the teenagers, and 12 normal people were selected. The first morning urine sample of each of the providers was collected, treated with protease inhibitor (1.67 ml of 100 mM NaN$_3$/2.5 ml of 10 mM PMSF/50 ul of 1 mM Leupeptin), and stored at −80° C. The urine sample was standardized with a urine creatinine level. The standardized urine sample [IgA nephropathy patients (IgAN): 88.1 ml, TGBM nephropathy patients (thinGBM): 65.2 ml] was used through a strong vortex action immediately after being dissolved, and clinicopathologic information of used urine is noted in Table 1.

TABLE 1

Clinicopathologic information on urine used for Example

|  | sex | age | Urine protein (/dl) | Ucr (/dl) | Histological classification |
|---|---|---|---|---|---|
| IgA nephropathy | M | 19 | 133 | 3423.0 | Haas subclassII |
|  | F | 18 | 80.5 | 1812.3 | Haas subclassII |
|  | F | 16 | 83.3 | 3891.3 | Haas subclassII |
|  | M | 19 | 31.8 | 4242.0 | Haas subclassII |
|  | M | 19 | 30.4 | 3513.3 | Haas subclassI |
|  | M | 19 | 40.9 | 5758.2 | TGBM |
| TGBM nephropathy | M | 19 | 32.3 | 3916.5 | TGBM |
|  | M | 19 | 30.0 | 4512.9 | TGBM |
|  | M | 19 | 43.6 | 5680.5 | TGBM |
|  | M | 18 | 34.5 | 3528.0 | TGBM |
|  | M | 18 | 28.8 | 2509.5 | TGBM |
|  | M | 19 | 31.0 | 5817.0 | TGBM |

Example 2

Purification of Exosome 2-1. Purification of Exosome

The urine creatinine level of each urine sample was recognized by a body fluid analyzer. Then, urine samples of three groups were put together after their volumes were set in such a manner that the same creatinine level was included. The put-together urine sample was subjected to first centrifugation (17,000 g for 15 min at 4° C.) to remove fragments such as whole cells or large membrane proteins. The supernatant of the first centrifugation was subjected to second centrifugation (200,000×g for 1 h at 4° C.) to precipitate low-density membrane vesicle protein. The precipitated resultant product was resuspended by using 50 ul of isolation buffer (250 mM sucrose/10 mM triethanolamine/0.5 mM PMSF/1 μM leupeptin), transferred to 1.5 ml polypropylene tube, added with 60 mg/ml of DTT, and reacted at 60° C. for 10 minutes to separate THP. Then, the isolation buffer was added to carry out centrifugation (200,000 g for 1 h at 4° C.), and thereby low-density membrane vesicle protein was precipitated and separated.

2-2. Confirmation of Exosome Purity

In order to confirm the purity of separated exosome, three fractions below were obtained: ① urinary sediment (obtained by carrying out first centrifugation (17.000×g, 15 minutes) of 10 ml of urine); ② urinary exosome (sediment which is obtained by carrying out first centrifugation (17,000×g, 15 minutes) of 10 ml of urine to provide supernatant, and then carrying out second centrifugation (200,000×g, 1 hour) of the supernatant); and ③ protein obtained by precipitating 10 ml of first centrifuged supernatant through the addition of the same amount of acetone thereto. The obtained fractions were loaded on 12% acrylamide gel, and subjected to electrophoresis. Protein of the gel was transferred to nitrocellulose membrane, and was subjected to western blot. The resultant product was subjected to blocking at room temperature for 1 hour in 5% non-skim milk dissolved in TBS-T (20 mM Tris, 500 mM NaCl, 0.05% Tween-20), added with 5% non-skim milk/TBS-T solution containing anti-AQP2 (aquapolin 2) (Santa Cruz, Calif., USA) as a marker protein of exosome, and anti-NHE3 (Na/H exchanger 3) (Chemicon, Temecula, Calif., USA) primary antibody, and reacted at 4° C. for 16 hours. Then, the resultant product was conjugated with a secondary antibody bound to horseradish peroxidase (Santa Cruz, Calif., USA) chemiluminescence (ECL, Amersham Pharmacia Biotech), and imaged by a sensing method. In order to confirm the separation purity of exosome, antibodies of two proteins (NHE3 and AQP2) as exosome marker proteins were used to carry out western blot on three fractions: ① urinary sediment (obtained by carrying out first centrifugation (17.000×g, 15 minutes) of 10 ml of urine); ② urinary exosome (sediment which is obtained by carrying out first centrifugation (17,000×g, 15 minutes) of 10 ml of urine to provide supernatant, and then carrying out second centrifugation (200,000×g, 1 hour) of the supernatant); and ③ protein obtained by precipitating 10 ml of first centrifuged supernatant through the addition of the same amount of acetone thereto. The result is shown in FIG. 1 {(A) Rabbit anti-Na+/H+ exchanger-3 [NHE-3] polyclonal antibody (B) Mouse anti-Aquaporin-2 [AQP-2] monoclonal antibody. (1) urinary sediment (pellet after 17,000 g 15 min spin); (2) urinary exosome (pellet after 200,000 g 1 hr spin from supernatant of 17,000 g 15 min spin) (3) a 10 ml aliquot of 17,000 g supernatant was used to isolate urinary protein by acetone precipitation.}. In the second fraction, two proteins as exosome markers were expressed, while in other two fractions, they were not expressed.

Example 3

Enzyme Digestion

The obtained exosome sediment was suspended in 14 ul of 0.3% SDS solution, mixed with 5 ul of acrylamide solution (30%), 0.7 ul of 1% ammonium persulfate, and 0.3 ul of TEMED, and polymerized at room temperature for about 30 minutes. A small gel was cut into pieces with a size of 1 mm$^3$ by a surgeon's knife, and washed with 25 mM of ABC buffer (pH 8.0) for 20 min and 25 mM of ABC (pH 8.0)/50% ACN buffer for 20 min. Then, the gel was dried by vacuum-drying, and subjected to a general in-gel digestion method. Each protein was added with 10 mM of DTT, reduced at 56° C. for 30 minutes, and then added with 55 mM of iodoacetamide (IAA), and alkylated by dark reaction at room temperature. Then, the gel pieces were washed with 25 mM of ABC (pH 8.0) buffer for 20 min and 25 mM of ABC (pH 8.0)/50% ACN buffer for 20 min, and dried by vacuum-drying. Trypsin was dissolved in 25 mM of ABC buffer to a concentration of 100 ng/ul, and reacted with gel pieces at 37° C. for 16 hours. Peptide cleaved by trypsin was extracted three times by using a solution of 25 mM ABC, 5% formic acid/25 mM ABC/50% ACN in water, and each extracted peptide solution was dried by vacuum-drying. Then, only peptide was collected by a solid-phase protein extracting method.

Example 4

Protein Identification

In nano-size liquid chromatography analysis, a nanoAcquity system (Waters Corporation, Milford, Mass.) was used, and herein, C18 trap column of 5 μm, 2 mm 180 μm (Symmetry), and C18 analyzing reversed-phase column of 1.7 μm, 25 cm×5 μm (BEH) (Waters Corporation) were used. The obtained peptide was analyzed by being dissolved in 0.1% formic acid. A mobile phase A (0.1% formic/water), and a mobile phase B (0.1% formic acid/CAN) were used. The phase was flowed into the trap column at a flow rate of 10 μL/min for 3 min. The mobile phase B was flowed at a concentration of 3 to 40% and a flow rate of 300 nl/min, for 360 min to separate peptide. The column was washed with 90% mobile phase B for 15 min, and then restabilized with 3% mobile phase B for 20 min. The temperature of the column was maintained at 35° C., and an auxiliary pump was used to move 100 fmol [Glu1]-Fibrinopeptide B/μL at a flow rate of 300 mL/min to a nano-lock reference spray of a mass spectrometer. All samples were repetitively carried out 4 times. The analysis of tryptic peptide was carried out by using Q-Tof Premier mass spectrometer (Waters Corporation, Manchester, UK). The mass spectrometer has a resolution of 10,000 FWHM in v-mode. All analyses were performed in a cation mode, and TOF analysis was carried out in a range of m/z 50~1990. [Glu1]-Fibrinopeptide B having a divalent charge was used to compensate an in-real time mass value, once per 30 sec. In low collision energy mass spectrometry, data is collected for 1 sec at 4 eV, and in high collision energy spectrometry, data is collected for 1 sec by increasing energy from 15 eV to 40 eV. Between the low collision energy spectrometry and the high collision energy spectrometry, there is a time difference of 0.1 sec.

Example 5

Relative Quantification

The data obtained by liquid-phase chromatography mass spectrometer was analyzed by using ProteinLynx GlobalServer v2.3 (Waters Corporation) software. From the clustered and normalized data, protein was identified by using an algorithm of ProteinLynx GlobalServer v2.3, and then the accurate mass value of the identified result and the delay time of the liquid-phase chromatography were used for clustering. The peak intensity of identified tryptic peptide was used to calculate the amount of each protein, and then the calculated value was used to determine the expression of protein in each group.

Example 6

Biomarker Validation

Figure 2:
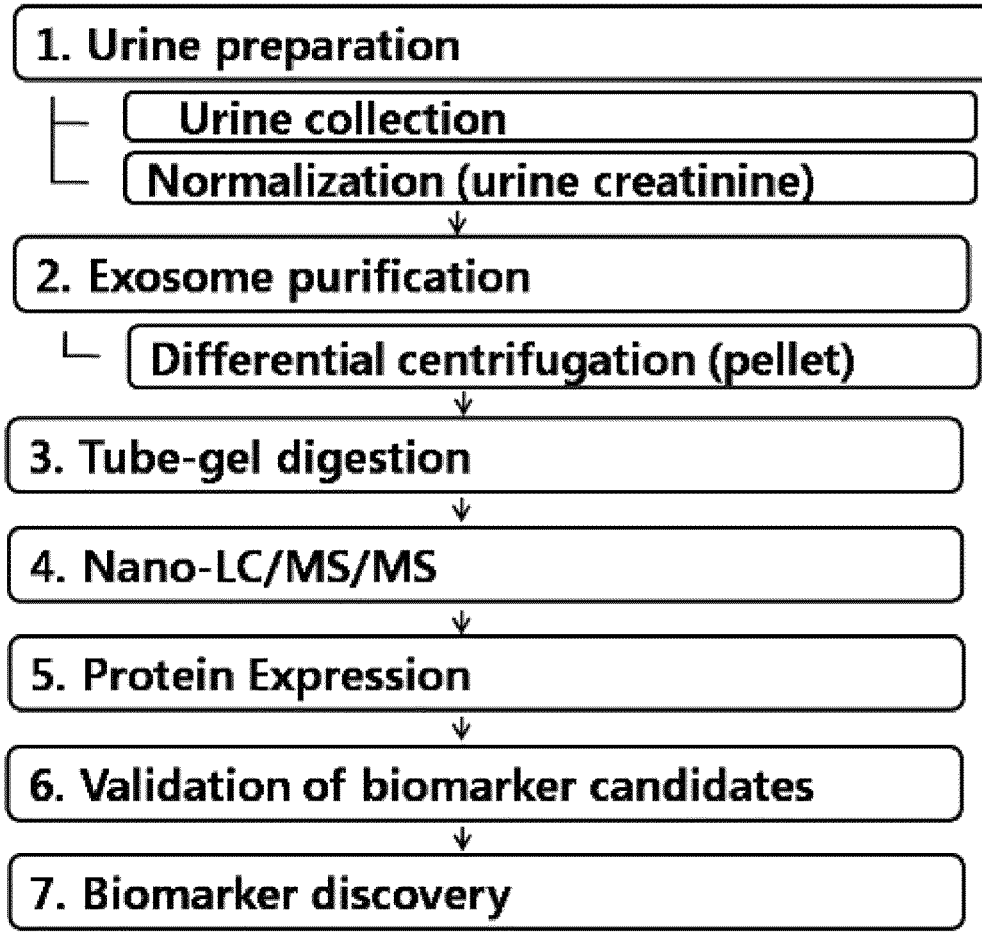
FIG. 2 is a flow chart showing a procedure for discovering a biomarker capable of diagnosing a disease from urine exosome.

From urine samples of 12 normal people, 5 IgA nephropathy patients, and 7 TGBM patients, exosomes were separated, and was subjected to western blot by using antibodies such as anti-Aminopeptidase N, anti-Vasorin precursor, anti-Ceruloplasmin, anti-Alpha-1-antitrypsin, to determine the expression extent of the protein in each group. The entire process for identifying a biomarker for diagnosing a disease from urinary exosome is shown in FIG. 2.

As a result of protein analysis in the above described Example, three repetitive tests through LC-MS/MS on a normal people group (a normal group) and two patient groups (IgAN group, and TGBM group) identified a total of 2059 proteins. Some of the proteins are noted in Tables 2 to 33.

TABLE 2

| Increased/decreased proteins identified by Example | | | | | | |
|---|---|---|---|---|---|---|
| Accession No. | Description | Score | Unique | Normal | IgAN | TGBM |
| IPI:IPI00000073.1 | EGF Pro-epidermal growth factor precursor | 1198.61 | | 1.00 | — | 1.19 |

TABLE 2-continued

Increased/decreased proteins identified by Example

| Accession No. | Description | Score | Unique | Normal | IgAN | TGBM |
|---|---|---|---|---|---|---|
| IPI:IPI00247063.3 | MME Neprilysin | 1112.42 | | 1.00 | — | 0.75 |
| IPI:IPI00788190.1 | EPS8L2 similar to epidermal growth factor receptor pathway substrate 8-like protein 2 | 851.67 | | 1.00 | — | 1.31 |
| IPI:IPI00017601.1 | CP Ceruloplasmin precursor | 742.16 | IgAN | — | IgAN_high | — |
| IPI:IPI00017367.6 | RDX Radixin isoform b | 728.13 | | 1.00 | — | 0.89 |
| IPI:IPI00022463.1 | TF Serotransferrin precursor | 711.44 | IgAN | — | IgAN_high | — |
| IPI:IPI00798430.1 | TF Transferrin variant (Fragment) | 711.44 | IgAN | — | IgAN_high | — |
| IPI:IPI00290337.7 | EPS8 Uncharacterized protein EPS8 | 707.62 | | 1.00 | — | 0.84 |
| IPI:IPI00008787.3 | NAGLU Alpha-N-acetylglucosaminidase precursor | 691.64 | Normal | Normal_high | — | — |
| IPI:IPI00339269.1 | HSPA6 Heat shock 70 kDa protein 6 | 690.55 | | 1.00 | — | 1.30 |
| IPI:IPI00220327.3 | KRT1 Keratin, type II cytoskeletal 1 | 679.34 | | 1.00 | 0.25 | 0.61 |
| IPI:IPI00295988.4 | PROM2 Prominin-2 | 669.97 | | 1.00 | — | 1.27 |
| IPI:IPI00246058.5 | PDCD6IP PDCD6IP protein | 669.19 | | 1.00 | 0.11 | 1.06 |
| IPI:IPI00871576.1 | PDCD6IP Dopamine receptor interacting protein 4 | 663.3 | | 1.00 | 0.11 | 1.07 |
| IPI:IPI00062047.5 | KIF12 Kinesin-like protein KIF12 | 657.26 | | 1.00 | — | 0.92 |

TABLE 3

Increased/decreased proteins identified by Example

| Accession No. | Description | Score | Unique | Normal | IgAN | TGBM |
|---|---|---|---|---|---|---|
| IPI:IPI00004573.2 | PIGR Polymeric immunoglobulin receptor precursor | 631.19 | | 1.00 | — | 0.93 |
| IPI:IPI00555656.1 | Huntingtin interacting protein-1-related (Fragment) | 621.62 | | 1.00 | — | 2.16 |
| IPI:IPI00746033.1 | NAGLU 47 kDa protein | 618.94 | | 1.00 | — | 1.55 |
| IPI:IPI00018953.1 | DPP4 Dipeptidyl peptidase 4 | 589.84 | | 1.00 | — | 0.79 |
| IPI:IPI00792032.1 | ABCB1 P-glycoprotein 1 | 581.18 | | 1.00 | — | 1.02 |
| IPI:IPI00027481.1 | ABCB1 Multidrug resistance protein 1 | 578.8 | | 1.00 | — | 0.74 |
| IPI:IPI00003765.1 | CAPN7 Calpain-7 | 547.66 | | 1.00 | — | 1.05 |
| IPI:IPI00177880.3 | PROM2 CDNA FLJ34089 fis, clone FCBBF3006249, moderately similar to Mus musculus prominin-like protein mRNA | 542.58 | | 1.00 | — | 1.17 |
| IPI:IPI00478530.1 | KIF12 Kinesin family member 12 | 539.36 | | 1.00 | — | 1.06 |
| IPI:IPI00794184.1 | CP 97 kDa protein | 535.08 | IgAN | — | IgAN_high | — |
| IPI:IPI00304925.5 | HSPA1A:HSPA1B Heat shock 70 kDa protein 1 | 519.91 | | 1.00 | — | 1.21 |
| IPI:IPI00847536.1 | HSPA1A:HSPA1B heat shock 70 kDa protein 1B | 519.91 | | 1.00 | — | 1.19 |
| IPI:IPI00845339.1 | HSPA1A:HSPA1B heat shock 70 kDa protein 1A | 519.91 | | 1.00 | — | 1.15 |
| IPI:IPI00746183.2 | UEVLD Isoform 1 of Ubiquitin-conjugating enzyme E2 variant 3 | 515.73 | | 1.00 | — | 0.92 |

TABLE 4

Increased/decreased proteins identified by Example

| Accession No. | Description | Score | Unique | Normal | IgAN | TGBM |
|---|---|---|---|---|---|---|
| IPI:IPI00005578.1 | EHD4 EH domain-containing protein 4 | 463.22 | | 1.00 | — | 1.09 |
| IPI:IPI00465028.7 | TPI1 Isoform 1 of Triosephosphate isomerase | 459.21 | | 1.00 | — | 0.99 |
| IPI:IPI00785050.1 | Putative uncharacterized protein | 458.65 | IgAN | — | IgAN_high | — |
| IPI:IPI00010418.4 | MYO1C Myosin-Ic | 455.53 | | 1.00 | — | 0.48 |
| IPI:IPI00216171.3 | ENO2 Gamma-enolase | 455 | | 1.00 | — | 0.71 |

TABLE 4-continued

Increased/decreased proteins identified by Example

| Accession No. | Description | Score | Unique | Normal | IgAN | TGBM |
|---|---|---|---|---|---|---|
| IPI:IPI00384697.2 | ALB Isoform 2 of Serum albumin precursor | 451.54 | | 1.00 | 4.00 | 1.86 |
| IPI:IPI00414315.8 | EPS8L2 Isoform 1 of Epidermal growth factor receptor kinase substrate 8-like protein 2 | 449.28 | | 1.00 | — | 1.51 |
| IPI:IPI00299088.3 | BAIAP2 Isoform 1 of Brain-specific angiogenesis inhibitor 1-associated protein 2 | 449.07 | | 1.00 | — | 3.00 |
| IPI:IPI00644120.1 | BAIAP2 Isoform 2 of Brain-specific angiogenesis inhibitor 1-associated protein 2 | 449.07 | | 1.00 | — | 2.77 |
| IPI:IPI00003269.1 | DKFZp686D0972 hypothetical protein LOC345651 | 447.24 | | 1.00 | — | 1.09 |
| IPI:IPI00553177.1 | SERPINA1 Isoform 1 of Alpha-1-antitrypsin precursor | 446.13 | IgAN | — | IgAN_high | — |
| IPI:IPI00873444.1 | RPS27A;UBC;UBB 79 kDa protein | 443.55 | | 1.00 | 0.20 | 0.83 |
| IPI:IPI00854806.1 | IGKV1-5 IGKV1-5 protein | 443.17 | | — | 1.00 | 0.64 |
| IPI:IPI00218407.6 | ALDOB Fructose-bisphosphate aldolase B | 442.98 | | 1.00 | — | 1.30 |

TABLE 5

Increased/decreased proteins identified by Example

| Accession No. | Description | Score | Unique | Normal | IgAN | TGBM |
|---|---|---|---|---|---|---|
| IPI:IPI00399007.5 | IGHG2 Putative uncharacterized protein DKFZp686I04196 (Fragment) | 441.69 | | — | 1.00 | 0.43 |
| IPI:IPI00644855.1 | C1orf58 Chromosome 1 open reading frame 58 | 437.68 | | 1.00 | — | 1.80 |
| IPI:IPI00337415.9 | GNAI1 Guanine nucleotide-binding protein G(i), alpha-1 subunit | 437.3 | | 1.00 | — | 1.07 |
| IPI:IPI00798127.1 | RPS27A; UBC; UBB ubiquitin C | 436.6 | | 1.00 | 0.16 | 0.85 |
| IPI:IPI00790784.2 | SERPINA1 Isoform 2 of Alpha-1-antitrypsin precursor | 435.08 | IgAN | — | IgAN_high | — |
| IPI:IPI00165579.6 | CNDP2 PP856 | 433.91 | | 1.00 | — | 1.13 |
| IPI:IPI00642333.1 | BAIAP2 Isoform 6 of Brain-specific angiogenesis inhibitor 1-associated protein 2 | 433.61 | | 1.00 | — | 2.69 |
| IPI:IPI00185159.7 | BAIAP2 Isoform 4 of Brain-specific angiogenesis inhibitor 1-associated protein 2 | 433.61 | | 1.00 | — | 1.46 |
| IPI:IPI00441344.1 | GLB1 Beta-galactosidase precursor | 433.01 | | 1.00 | — | 0.77 |
| IPI:IPI00797646.3 | GLB1 Beta-galactosidase (Fragment) | 433.01 | | 1.00 | — | 0.50 |
| IPI:IPI00479743.3 | POTE2 protein expressed in prostate, ovary, testis, and placenta 2 | 432.29 | | 1.00 | — | 1.21 |
| IPI:IPI00180292.5 | BAIAP2 Isoform 5 of Brain-specific angiogenesis inhibitor 1-associated protein 2 | 431.62 | | 1.00 | — | 1.15 |
| IPI:IPI00785200.1 | Putative uncharacterized protein | 430.24 | IgAN | — | IgAN_high | — |
| IPI:IPI00739539.5 | LOC728378 Chimeric POTE-actin protein | 428.33 | | 1.00 | — | 1.28 |

TABLE 6

Increased/decreased proteins identified by Example

| Accession No. | Description | Score | Unique | Normal | IgAN | TGBM |
|---|---|---|---|---|---|---|
| IPI:IPI00004503.5 | LAMP1 lysosomal-associated membrane protein 1 | 426.54 | | 1.00 | — | 1.00 |
| IPI:IPI00305457.5 | SERPINA1 PRO2275 | 424.86 | | 1.00 | 3.23 | — |
| IPI:IPI00647603.1 | BAIAP2 Isoform 3 of Brain-specific angiogenesis inhibitor 1-associated protein 2 | 424.12 | | 1.00 | — | 0.76 |
| IPI:IPI00219365.3 | MSN Moesin | 423.34 | | 1.00 | — | 0.92 |
| IPI:IPI00872814.1 | MSN 68 kDa protein | 423.34 | | 1.00 | — | 0.88 |
| IPI:IPI00217906.3 | GNAI2 Isoform 2 of Guanine nucleotide-binding protein G(i), alpha-2 subunit | 421.08 | | 1.00 | — | 0.97 |
| IPI:IPI00555945.1 | IGL@ IGL@ protein | 420.93 | IgAN | — | IgAN_high | — |
| IPI:IPI00217342.8 | UEVLD Isoform 2 of Ubiquitin-conjugating enzyme E2 variant 3 | 420.53 | | 1.00 | — | 0.95 |
| IPI:IPI00027438.2 | FLOT1 Flotillin-1 | 419.67 | Normal | Normal_high | — | — |
| IPI:IPI00217717.2 | GGT1 Isoform 2 of Gamma-glutamyl transpeptidase 1 precursor | 419.38 | | 1.00 | — | 0.69 |
| IPI:IPI00646907.1 | SLC12A3 solute carrier family 12 (sodium/chloride transporters), member 3 | 418.98 | | 1.00 | — | 0.64 |
| IPI:IPI00216438.3 | SLC12A3 Solute carrier family 12 member 3 | 418.98 | | 1.00 | — | 0.24 |
| IPI:IPI00816555.1 | IGLV2-14 IGLV2-14 protein | 418.93 | IgAN | — | IgAN_high | — |
| IPI:IPI00719452.1 | IGL@ IGL@ protein | 415.4 | IgAN | — | IgAN_high | — |
| IPI:IPI00007682.2 | ATP6V1A Vacuolar ATP synthase catalytic subunit A | 415.25 | Normal | Normal_high | — | — |

TABLE 7

Increased/decreased proteins identified by Example

| Accession No. | Description | Score | Unique | Normal | IgAN | TGBM |
|---|---|---|---|---|---|---|
| IPI:IPI00420088.1 | KIAA0174 Isoform 2 of Uncharacterized protein KIAA0174 | 415.06 | | 1.00 | 0.14 | 1.46 |
| IPI:IPI00829626.1 | IGL@ IGL@ protein | 414.97 | IgAN | — | IgAN_high | — |
| IPI:IPI00218343.4 | TUBA1C Tubulin alpha-1C chain | 413.63 | | 1.00 | — | 0.66 |
| IPI:IPI00873229.1 | UEVLD 42 kDa protein | 412.57 | | 1.00 | — | 1.02 |
| IPI:IPI00382938.3 | IGLV4-3 IGLV4-3 protein | 411.54 | IgAN | — | IgAN_high | — |
| IPI:IPI00003362.2 | HSPA5 HSPA5 protein | 410.4 | TGBM | — | — | TGBM_high |
| IPI:IPI00024660.1 | KIAA0174 Isoform 1 of Uncharacterized protein KIAA0174 | 409.31 | | 1.00 | 0.17 | 1.58 |
| IPI:IPI00386516.3 | KIAA0174 KIAA0174 protein | 409.31 | | 1.00 | 0.16 | 1.57 |
| IPI:IPI00550162.2 | IGLV3-25 IGLV3-25 protein | 408.52 | IgAN | — | IgAN_high | — |
| IPI:IPI00797510.1 | GNAI2 35 kDa protein | 408.48 | | 1.00 | — | 1.01 |
| IPI:IPI00798391.1 | GNAI2 39 kDa protein | 408.48 | | 1.00 | — | 0.97 |
| IPI:IPI00794986.1 | GNAI2 WUGSC: H_LUCA15.1 protein | 408.48 | | 1.00 | — | 0.95 |
| IPI:IPI00025476.1 | AMY1A; AMY1C; AMY2A; AMY1B Pancreatic alpha-amylase precursor | 407.93 | | 1.00 | — | 4.06 |
| IPI:IPI00867501.1 | TUBA1B similar to Tubulin alpha-ubiquitous chain | 407.67 | | 1.00 | — | 0.79 |
| IPI:IPI00387144.4 | TUBA1B Tubulin alpha-1B chain | 407.67 | | 1.00 | — | 0.77 |
| IPI:IPI00792677.1 | TUBA1B 46 kDa protein | 407.67 | | 1.00 | — | 0.56 |

TABLE 8

Increased/decreased proteins identified by Example

| Accession No. | Description | Score | Unique | Normal | IgAN | TGBM |
|---|---|---|---|---|---|---|
| IPI:IPI00658130.1 | IGL@ IGL@ protein | 396.3 | IgAN | — | IgAN_high | — |
| IPI:IPI00555577.1 | THY 1 Thy-1 cell surface antigen variant (Fragment) | 395.31 | | 1.00 | — | 0.60 |
| IPI:IPI00478908.3 | TUBA1C 29 kDa protein | 394.78 | | 1.00 | — | 0.78 |
| IPI:IPI00018434.1 | TSG101 Isoform 1 of Tumor susceptibility gene 101 protein | 394.12 | | 1.00 | — | 0.76 |
| IPI:IPI00718819.2 | IGLC3; IGLV2-14; IGLC2; IGLC1; IGL@ IGLV2-14 protein | 394.07 | IgAN | — | IgAN_high | — |
| IPI:IPI00795257.1 | GAPDH 32 kDa protein | 393.43 | | 1.00 | — | 0.85 |
| IPI:IPI00807428.1 | Putative uncharacterized protein | 393.17 | IgAN | — | IgAN_high | — |
| IPI:IPI00830047.1 | Uncharacterized protein ENSP00000374858 (Fragment) | 391.69 | IgAN | — | IgAN_high | — |
| IPI:IPI00827875.1 | Lambda-chain precursor | 390.42 | IgAN | — | IgAN_high | — |
| IPI:IPI00744476.6 | IGL@ IGL@ protein | 388.78 | IgAN | — | IgAN_high | — |
| IPI:IPI00784935.1 | Putative uncharacterized protein | 388.78 | IgAN | — | IgAN_high | — |
| IPI:IPI00789134.1 | GAPDH Glyceraldehyde 3-phosphate dehydrogenase | 388.29 | | 1.00 | — | 0.96 |
| IPI:IPI00218414.5 | CA2 Carbonic anhydrase 2 | 387.66 | | 1.00 | — | 0.89 |
| IPI:IPI00740545.1 | LOC653269 similar to Prostate, ovary, testis expressed protein on chromosome 2 isoform 2 | 387.64 | | 1.00 | — | 0.79 |
| IPI:IPI00218474.5 | ENO3 Beta-enolase | 386.68 | | 1.00 | — | 3.63 |

TABLE 9

Increased/decreased proteins identified by Example

| Accession No. | Description | Score | Unique | Normal | IgAN | TGBM |
|---|---|---|---|---|---|---|
| IPI:IPI00647012.1 | HSPA1A; HSPA1B Heat shock 70 kDa protein 1A | 367.55 | Normal | Normal_high | — | — |
| IPI:IPI00473011.3 | HBD; HBB Hemoglobin subunit delta | 366.74 | | — | 1.00 | 4.85 |
| IPI:IPI00478003.1 | A2M Alpha-2-macroglobulin precursor | 364.04 | IgAN | — | IgAN_high | — |
| IPI:IPI00441550.1 | GLB1 Beta-galactosidase-related protein precursor | 362.89 | | 1.00 | — | 0.57 |
| IPI:IPI00022892.2 | THY 1 Thy-1 membrane glycoprotein precursor | 361.81 | | 1.00 | — | 0.59 |
| IPI:IPI00797221.3 | GAPDH Glyceraldehyde-3-phosphate dehydrogenase | 360.95 | | 1.00 | — | 0.84 |
| IPI:IPI00182728.2 | VPS4B Vasculor protein sorting-associating protein 4B | 360.67 | | 1.00 | 0.07 | 0.78 |
| IPI:IPI00289983.3 | ACPP ACPP protein | 358.26 | Normal | Normal_high | — | — |
| IPI:IPI00384938.1 | IGHG1 Putative uncharacterized protein DKFZp686N02209 | 358.13 | | — | 1.00 | 0.94 |
| IPI:IPI00065500.3 | C1orf58 BRO1 domain-containing protein BROX | 357.19 | | 1.00 | — | 1.08 |
| IPI:IPI00789376.1 | KNG1 KNG1 protein | 356.73 | | 1.00 | — | 0.83 |
| IPI:IPI00383071.1 | LOC729708 Triosephosphate isomerase (Fragment) | 355.76 | | 1.00 | — | 0.86 |
| IPI:IPI00396434.1 | ACPP Prostatic acid phosphatase precursor | 354.4 | Normal | Normal_high | — | — |
| IPI:IPI00423463.1 | IGHG1 Putative uncharacterized protein DKFZp686O01196 | 354.2 | | — | 1.00 | 0.95 |

TABLE 10

Increased/decreased proteins identified by Example

| Accession No. | Description | Score | Unique | Normal | IgAN | TGBM |
|---|---|---|---|---|---|---|
| IPI:IPI00787680.1 | similar to Triosephosphate isomerase (TIM) (Triose-phosphate isomerase) isoform 2 | 353.67 | | 1.00 | — | 0.97 |
| IPI:IPI00790896.1 | GNB2 26 kDa protein | 351.94 | | 1.00 | — | 1.16 |
| IPI:IPI00829944.1 | IGHG1 IGHG1 protein | 350.78 | | — | 1.00 | 0.90 |
| IPI:IPI00872379.1 | ANXA5 36 kDa protein | 350.57 | | 1.00 | — | 0.59 |
| IPI:IPI00329801.12 | ANXA5 Annexin A5 | 350.57 | | 1.00 | — | 0.58 |
| IPI:IPI00829767.1 | IGHG2 Uncharacterized protein IGHG2 (Fragment) | 350.51 | | — | 1.00 | 0.44 |
| IPI:IPI00423466.1 | IGHG1 Putative uncharacterized protein DKFZp686H20196 | 348.53 | | 1.00 | 4.76 | 4.31 |
| IPI:IPI00790302.1 | GNB2 28 kDa protein | 347.94 | | 1.00 | — | 1.19 |
| IPI:IPI00011134.2 | HSPA7 Putative heat shock 70 kDa protein 7 | 347.71 | | 1.00 | — | 1.34 |
| IPI:IPI00796250.1 | GNAI2 27 kDa protein | 346.68 | | 1.00 | — | 0.97 |
| IPI:IPI00872328.1 | HBB Beta-globin gene from a thalassemia patient | 345.5 | | — | 1.00 | 4.84 |
| IPI:IPI00784817.1 | Anti-RhD monoclonal T125 gamma 1 heavy chain precursor | 344.56 | | 1.00 | 4.35 | 4.26 |
| IPI:IPI00761159.1 | IGHM IGHM protein | 343.37 | | 1.00 | 4.76 | 4.06 |
| IPI:IPI00807531.2 | IGHG1 IGHG1 protein | 342.47 | | — | 1.00 | 0.79 |

TABLE 11

Increased/decreased proteinsidentified by Example

| Accession No. | Description | Score | Unique | Normal | IgAN | TGBM |
|---|---|---|---|---|---|---|
| IPI:IPI00796636.8 | HBB Hemoglobin (Fragment) | 340.64 | | — | 1.00 | 4.81 |
| IPI:IPI00293088.4 | GAA Uncharacterized protein GAA | 340.59 | TGBM | — | — | TGBM_high |
| IPI:IPI00398700.3 | GNAO1 Guanine nucleotide-binding protein G(o) subunit alpha 2 | 340.2 | | 1.00 | — | 1.05 |
| IPI:IPI00784828.1 | Putative Uncharacterized protein DKFZp686C11235 | 339.74 | | 1.00 | 4.76 | 4.18 |
| IPI:IPI00815926.1 | IGHG1 IGHG1 protein | 339.65 | | 1.00 | 5.26 | 4.71 |
| IPI:IPI00004101.4 | BHMT Betaine-homocysteine S-methyltransferase 1 | 339.64 | | 1.00 | — | 0.93 |
| IPI:IPI00513830.1 | ALDOB Fructose-bisphosphate aldolase | 339.19 | | 1.00 | — | 1.32 |
| IPI:IPI00024403.1 | CPNE3 Copine-3 | 336.53 | | 1.00 | — | 0.82 |
| IPI:IPI00448925.3 | IGHG1 IGHG1 protein | 336.47 | | — | 1.00 | 0.90 |
| IPI:IPI00743241.1 | RPS27A; UBC; UBB 44 kDa protein | 335.03 | | 1.00 | 0.19 | 0.84 |
| IPI:IPI00743650.1 | RPS27A; UBC; UBB 44 kDa protein | 335.03 | | 1.00 | 0.18 | 0.84 |
| IPI:IPI00784810.1 | IGHV4-31 protein | 333.43 | | 1.00 | 4.17 | 3.74 |
| IPI:IPI00465248.5 | ENO1 Isoform alpha-enolase of Alpha-enolase | 333.4 | | 1.00 | — | 0.79 |
| IPI:IPI00744274.1 | RPS27A; UBC; UBB 44 kDa protein | 332.81 | | 1.00 | 0.19 | 0.83 |
| IPI:IPI00645363.2 | IGHG1 Putative uncharacterized protein DKFZp686P15220 | 332.5 | | — | 1.00 | 0.93 |

TABLE 12

Increased/decreased proteins identified by Example

| Accession No. | Description | Score | Unique | Normal | IgAN | TGBM |
|---|---|---|---|---|---|---|
| IPI:IPI00423464.1 | IGHG1 Putative uncharacterized protein DKFZp686K03196 | 332.27 | | — | 1.00 | 0.90 |
| IPI:IPI00448938.1 | IGHG1 IGHG1 protein | 332.07 | | — | 1.00 | 0.90 |
| IPI:IPI00013769.1 | Alpha-enolase, lung specific | 330.56 | | 1.00 | — | 1.36 |
| IPI:IPI00784822.1 | IGHV4-31 IGHV4-31 protein | 330.18 | | — | 1.00 | 0.90 |
| IPI:IPI00335421.4 | FIGNL1 Isoform 1 of Fidgetin-like protein 1 | 330.14 | | 1.00 | — | 0.78 |
| IPI:IPI00221224.6 | ANPEP Aminopeptidase N | 328.19 | | 1.00 | 0.05 | 0.65 |
| IPI:IPI00784842.1 | IGHV4-31 Putative uncharacterized protein DKFZp686G11190 | 327.93 | | — | 1.00 | 0.91 |
| IPI:IPI00792712.1 | RPS27A; UBC; UBB 39 kDa protein | 327.63 | | 1.00 | 0.19 | 0.84 |
| IPI:IPI00009030.1 | LAMP2 Isoform LAMP-2A of Lysosome-associated membrane glycoprotein 2 precursor | 327.49 | Normal | Normal_high | — | — |
| IPI:IPI00216172.2 | LAMP2 Lysosomal-associated membrane protein 2C | 327.49 | Normal | Normal_high | — | — |
| IPI:IPI00739827.1 | LAMP2 Isoform LAMP-2B of Lysosome-associated membrane glycoprotein 2 precursor | 327.49 | Normal | Normal_high | — | — |
| IPI:IPI00816681.1 | IGHM Hepatitis B virus receptor binding protein (Fragment) | 322.91 | | 1.00 | 5.00 | 4.44 |
| IPI:IPI00220281.3 | GNAO1 Guanine nucleotide-binding protein G(o) subunit alpha 1 | 322.25 | | 1.00 | — | 1.11 |

TABLE 13

Increased/decreased proteins identified by Example

| Accession No. | Description | Score | Unique | Normal | IgAN | TGBM |
|---|---|---|---|---|---|---|
| IPI:IPI00794035.1 | GNAI2 20 kDa protein | 311.97 | | 1.00 | — | 1.00 |
| IPI:IPI00795746.1 | GNAI2 19 kDa protein | 311.97 | | 1.00 | — | 0.95 |
| IPI:IPI00400826.1 | CLU clusterin isoform 1 | 311.5 | TGBM | — | — | TGBM_high |
| IPI:IPI00418813.2 | CDNA FLJ46113 fis, clone TESTI2036285, highly similar to Rattus norvegicus ubiquitin C | 311.25 | | 1.00 | 0.18 | 0.72 |
| IPI:IPI00785079.1 | Putative Uncharacterized protein | 310.01 | IgAN | — | IgAN_high | — |
| IPI:IPI00784589.1 | Putative Uncharacterized protein DKFZp781M0386 | 309.1 | IgAN | — | IgAN_high | — |
| IPI:IPI00829640.1 | IGL@ IGL@ protein | 309.01 | IgAN | — | IgAN_high | — |
| IPI:IPI00855706.1 | FIGNL1 Isoform 2 of Fidgetin-like protein 1 | 307.57 | | 1.00 | — | 0.68 |
| IPI:IPI00784711.1 | Putative Uncharacterized protein | 307.48 | IgAN | — | IgAN_high | — |
| IPI:IPI00031821.1 | ITM2B Integral membrane protein 2B | 306.68 | | 1.00 | — | 0.64 |
| IPI:IPI00719373.1 | IGL@ IGL@ protein | 306.35 | IgAN | — | IgAN_high | — |
| IPI:IPI00479186.5 | PKM2 Isoform M2 of Pyruvate kinase isozymes M1/M2 | 303.28 | TGBM | — | — | TGBM_high |
| IPI:IPI00789902.1 | GPRC5C G protein-coupled receptorr family C, group 5, member C isoform b | 302.78 | | 1.00 | 0.12 | 1.36 |

TABLE 14

Increased/decreased proteins identified by Example

| Accession No. | Description | Score | Unique | Normal | IgAN | TGBM |
|---|---|---|---|---|---|---|
| IPI:IPI00719280.2 | RPS27A; UBC; UBB ubiquitin B precursor | 290.53 | | 1.00 | 0.19 | 0.84 |
| IPI:IPI00798155.3 | RPS27A; UBC; UBB Ubiquitin C splice variant | 290.53 | | 1.00 | 0.18 | 0.82 |
| IPI:IPI00423461.3 | IGHA2 Putative uncharacterized protein DKFZp686C02220 (Fragment) | 290.26 | | 1.00 | 0.99 | 1.39 |
| IPI:IPI00852577.1 | IGLC1 protein | 289.84 | IgAN | — | IgAN_high | — |
| IPI:IPI00847989.1 | PKM2 Pyruvate kinase (Fragment) | 289.12 | | 1.00 | — | 1.43 |
| IPI:IPI00791026.1 | MYO1C 56 kDa protein | 289.07 | | 1.00 | — | 0.81 |
| IPI:IPI00180675.4 | TUBA1A Tubulin alpha-1A chain | 285.54 | | 1.00 | — | 0.75 |
| IPI:IPI00794663.1 | TUBA4A 48 kDa protein | 284.61 | Normal | Normal_high | — | — |
| IPI:IPI00007750.1 | TUBA4A Tubulin alpha-4A chain | 284.61 | Normal | Normal_high | — | — |
| IPI:IPI00790633.1 | RPS27A; UBC; UBB 25 kDa protein | 282.66 | | 1.00 | 0.19 | 0.83 |
| IPI:IPI00646909.2 | TUBA8 Tubulin alpha-8 chain | 282.44 | Normal | Normal_high | — | — |
| IPI:IPI00787871.1 | LOC729708 similar to Triosephosphate isomerase (TIM) (Triose-phosphate isomerase) isoform 1 | 281.63 | | 1.00 | — | 0.84 |
| IPI:IPI00007221.1 | SERPINA5 Plasma serine protease inhibitor precursor | 280.84 | | 1.00 | — | 0.67 |

TABLE 15

Increased/decreased proteins identified by Example

| Accession No. | Description | Score | Unique | Normal | IgAN | TGBM |
|---|---|---|---|---|---|---|
| IPI:IPI00642117.4 | GNB1 Beta-subunit signal transducing proteins GS/GI | 280.41 | | 1.00 | — | 1.13 |
| IPI:IPI00793953.1 | TUBA8 Putative uncharacterized protein DKFZp686L04275 (Fragment) | 280.05 | Normal | Normal_high | — | — |
| IPI:IPI00787104.1 | similar to Triosephosphate isomerase (TIM) (Triose-phosphate isomerase) isoform 1 | 279.54 | | 1.00 | — | 0.84 |
| IPI:IPI00827694.1 | UEVLD Isoform 4 of Ubiquitin-conjugating enzyme E2 variant 3 | 279.48 | | 1.00 | — | 0.99 |
| IPI:IPI00031065.1 | DNASE1 Deoxyribonuclease-1 precursor | 279.47 | TGBM | — | — | TGBM_high |
| IPI:IPI00794925.1 | RPS27A; UBC; UBB 21 kDa protein | 279.06 | | 1.00 | 0.19 | 0.82 |
| IPI:IPI00295414.7 | COL15A1 Collagen alpha-1 (XV) chain precursor | 278.78 | | 1.00 | — | 1.99 |
| IPI:IPI00795527.1 | RPS27A; UBC; UBB 21 kDa protein | 278.08 | | 1.00 | 0.19 | 0.81 |
| IPI:IPI00737216.1 | LOC652899 similar to Salivary alpha-amylase precursor | 277.03 | | 1.00 | — | 3.67 |
| IPI:IPI00797969.1 | GNB2 17 kDa protein | 275.94 | | 1.00 | — | 1.11 |
| IPI:IPI00291928.8 | RAB14 Ras-related protein Rab-14 | 275.03 | | 1.00 | — | 1.11 |
| IPI:IPI00792478.1 | TUBA8 43 kDa protein | 274.85 | Normal | Normal_high | — | — |
| IPI:IPI00639998.1 | GNB1 Guanine nucleotide binding protein (G protein), beta polypeptide 1 | 274.52 | | 1.00 | — | 1.15 |

TABLE 16

Increased/decreased proteins identified by Example

| Accession No. | Description | Score | Unique | Normal | IgAN | TGBM |
|---|---|---|---|---|---|---|
| IPI:IPI00657660.1 | HBB Hemoglobin delta-beta fusion protein | 273.87 | | — | 1.00 | 4.62 |
| IPI:IPI00829877.1 | IGL@ IGL@ protein | 272.78 | IgAN | — | IgAN_high | — |
| IPI:IPI00095891.2 | GNAS Isoform XLas-1 of Guanine nucleotide-binding protein G(s) subunit alpha isoforms XLas | 271.41 | TGBM | — | — | TGBM_high |
| IPI:IPI00556204.1 | Eukaryotic translation elongation factor 1 alpha 2 variant (Fragment) | 270.05 | | 1.00 | — | 3.35 |
| IPI:IPI00218164.1 | MUC1 Isoform 3 of Mucin-1 precursor | 269.65 | | — | 1.00 | 8.85 |
| IPI:IPI00788932.1 | GNAL Guanine nucleotide binding protein | 269.18 | TGBM | — | — | TGBM_high |
| IPI:IPI00796600.1 | RPS27A; UBC; UBB 18 kDa protein | 267.56 | | 1.00 | 0.19 | 0.83 |
| IPI:IPI00867545.1 | MUC1 isoform M6 | 267.43 | | 1.00 | — | 0.75 |
| IPI:IPI00793810.1 | RPS27A; UBC; UBB 19 kDa protein | 266.84 | | 1.00 | 0.19 | 0.82 |
| IPI:IPI00796007.1 | RPS27A; UBC; UBB 17 kDa protein | 264.75 | | 1.00 | 0.19 | 0.84 |
| IPI:IPI00797400.1 | RPS27A; UBC; UBB 19 kDa protein | 264.75 | | 1.00 | 0.19 | 0.81 |
| IPI:IPI00794211.1 | RPS27A; UBC; UBB 18 kDa protein | 264.75 | | 1.00 | 0.19 | 0.80 |
| IPI:IPI00830113.2 | HBB 19 kDa protein | 264.14 | | — | 1.00 | 5.26 |
| IPI:IPI00789823.1 | RPS27A; UBC; UBB 16 kDa protein | 263.36 | | 1.00 | 0.19 | 0.82 |
| IPI:IPI00640949.1 | GNB1 Guanine nucleotide binding protein (G protein), beta polypeptide 1 | 263.01 | | 1.00 | — | 1.20 |

TABLE 17

Increased/decreased proteins identified by Example

| Accession No. | Description | Score | Unique | Normal | IgAN | TGBM |
|---|---|---|---|---|---|---|
| IPI:IPI00640462.1 | GNB1 Guanine nucleotide binding protein (G protein), beta polypeptide 1 | 261.63 | | 1.00 | — | 1.13 |
| IPI:IPI00784990.2 | RPS27A; UBC; UBB Ubiquitin C splice variant | 261.51 | | 1.00 | 0.19 | 0.84 |
| IPI:IPI00012451.3 | GNB4 Guanine nucleotide-binding protein subunit beta-4 | 260.68 | | 1.00 | — | 1.13 |
| IPI:IPI00645255.1 | GDI2 GDP dissociation inhibitor 2 | 260.03 | Normal | Normal_high | — | — |
| IPI:IPI00218163.1 | MUC1 Isoform 2 of Mucin-1 precursor | 257.97 | | — | 1.00 | 8.58 |
| IPI:IPI00218165.1 | MUC1 Isoform 4 of Mucin-1 precursor | 257.97 | | — | 1.00 | 8.33 |
| IPI:IPI00013955.1 | MUC1 Isoform 1 of Mucin-1 precursor | 257.97 | | — | 1.00 | 8.33 |
| IPI:IPI00607844.1 | MUC1 Mucin 1, cell surface associated | 257.97 | | 1.00 | 0.10 | 0.92 |
| IPI:IPI00829896.1 | HBD Hemoglobin Lepore-Baltimore (Fragment) | 255.62 | | — | 1.00 | 4.71 |
| IPI:IPI00816229.1 | ACTA2 ACTA2 protein (Fragment) | 255.2 | | 1.00 | 0.15 | 1.26 |
| IPI:IPI00291866.5 | SERPING1 Plasma protease C1 inhibitor precursor | 252.16 | | 1.00 | — | 1.97 |

TABLE 18

Increased/decreased proteins identified by Example

| Accession No. | Description | Score | Unique | Normal | IgAN | TGBM |
|---|---|---|---|---|---|---|
| IPI:IPI00556287.1 | Putative Uncharacterized protein | 250.96 | | — | 1.00 | 0.79 |
| IPI:IPI00793848.1 | CLU 54 kDa protein | 249.02 | TGBM | — | — | TGBM_high |
| IPI:IPI00794488.1 | GNAI2 12 kDa protein | 248.73 | | 1.00 | — | 0.80 |
| IPI:IPI00013945.1 | UMOD Isoform 1 of Uromodulin precursor | 248.09 | | 1.00 | 0.76 | 1.34 |
| IPI:IPI00640271.1 | UMOD 74 kDa protein | 248.09 | | 1.00 | 0.74 | 1.34 |
| IPI:IPI00032561.1 | CAB39 Calcium-binding protein 39 | 247.93 | Normal | Normal_high | — | — |
| IPI:IPI00793330.1 | RPS27A; UBC; UBB 12 kDa protein | 247.23 | | 1.00 | 0.17 | 0.82 |
| IPI:IPI00456429.3 | UBA52 ubiquitin and ribosomal protein L40 precursor | 246.39 | | 1.00 | 0.19 | 0.81 |
| IPI:IPI00759806.1 | ENO1 Isoform MBP-1 of Alpha-enolase | 246.28 | | 1.00 | — | 1.46 |
| IPI:IPI00008964.3 | RAB1B Ras-related protein Rab-1B | 245.38 | | 1.00 | — | 0.71 |
| IPI:IPI00300562.2 | RAB3B Ras-related protein Rab-3B | 245.02 | | 1.00 | — | 0.99 |
| IPI:IPI00737338.1 | UMOD Isoform 2 of Uromodulin precursor | 244.98 | | 1.00 | 0.88 | 1.21 |
| IPI:IPI00744076.1 | UMOD Isoform 3 of Uromodulin precursor | 244.45 | | 1.00 | 0.82 | 1.35 |
| IPI:IPI00179330.6 | RPS27A; UBC; UBB ubiquitin and ribosomal protein S27a precursor | 244.41 | | 1.00 | 0.19 | 0.82 |

TABLE 19

Increased/decreased proteins identified by Example

| Accession No. | Description | Score | Unique | Normal | IgAN | TGBM |
|---|---|---|---|---|---|---|
| IPI:IPI00795461.1 | CAPN7 18 kDa protein | 243.8 | | 1.00 | — | 0.73 |
| IPI:IPI00646415.1 | RAB14 20 kDa protein | 243.75 | | 1.00 | — | 0.98 |
| IPI:IPI00654754.1 | RPS27A; UBC; UBB RPS27A protein | 243.53 | | 1.00 | 0.20 | 0.93 |
| IPI:IPI00556549.1 | SERPING1 Serine/cysteine proteinase inhibitor clade G member 1 splice variant 2 (Fragment) | 243.4 | | 1.00 | — | 1.92 |
| IPI:IPI00395488.2 | VASN Vasorin precursor | 242.49 | | 1.00 | — | 3.49 |
| IPI:IPI00008603.1 | ACTA2 Actin, aortic smooth muscle | 240.99 | | 1.00 | 0.08 | 1.26 |
| IPI:IPI00792139.1 | RPS27A; UBC; UBB 9 kDa protein | 240.24 | | 1.00 | 0.18 | 0.93 |
| IPI:IPI00646491.2 | GNAS Isoform XLas-2 of Guanine nucleotide-binding protein G(s) subunit alpha isoforms XLas | 239.84 | TGBM | — | — | TGBM_high |
| IPI:IPI00004416.1 | CHMP2A Charged multivesicular body protein 2a | 239.77 | | 1.00 | — | 0.95 |
| IPI:IPI00478874.1 | SDCBP syntenin isoform 2 | 239.64 | | 1.00 | 0.08 | 0.95 |
| IPI:IPI00869217.1 | LOC645367 Similar to Gamma-glutamyltranspeptidase 1 precursor (EC 2.3.2.2) (Gammaglutamyltransferase 1) (CD224 antigen) [Contains: Gammaglutamyltranspeptidase 1 heavy chain; Gamma-glutamyltranspeptidase 1 light chain]. Isoform 2 | 238.89 | | 1.00 | — | 0.64 |

TABLE 20

Increased/decreased proteins identified by Example

| Accession No. | Description | Score | Unique | Normal | IgAN | TGBM |
|---|---|---|---|---|---|---|
| IPI:IPI00607569.1 | MUC1 mucin 1 isoform 2 precursor | 238.62 | | 1.00 | 0.14 | 1.23 |
| IPI:IPI00607673.2 | MUC1 MUC1 isoform Z-LSP | 238.62 | | 1.00 | 0.13 | 1.19 |
| IPI:IPI00385173.2 | MUC1 mucin 1 isoform 3 precursor | 238.62 | | 1.00 | 0.13 | 1.14 |
| IPI:IPI00218170.1 | MUC1 Isoform 8 of Mucin-1 precursor | 238.62 | | 1.00 | 0.11 | 0.96 |
| IPI:IPI00218169.1 | MUC1 Isoform 7 of Mucin-1 precursor | 238.62 | | 1.00 | 0.11 | 0.95 |
| IPI:IPI00873004.1 | UBA52 11 kDa protein | 237.63 | | 1.00 | 0.20 | 0.93 |
| IPI:IPI00382606.1 | F7 Factor VII active site mutant immunoconjugate | 236.89 | IgAN | — | IgAN_high | — |
| IPI:IPI00657915.1 | EHD1 41 kDa protein | 236.83 | Normal | Normal_high | — | — |
| IPI:IPI00216791.2 | SLC12A1 SLC12A1 protein | 236.5 | | 1.00 | — | 1.12 |
| IPI:IPI00745461.1 | VASN Uncharacterized protein VASN | 235.47 | | 1.00 | — | 3.29 |
| IPI:IPI00419932.4 | RAB12 Putative Ras-related protein Rab-12 | 235.04 | | 1.00 | — | 1.55 |
| IPI:IPI00025416.3 | ACTG2 Actin, gamma-enteric smooth muscle | 234.71 | | 1.00 | 0.08 | 1.26 |
| IPI:IPI00218168.1 | MUC1 Isoform 6 of Mucin-1 precursor | 232.19 | | 1.00 | 0.10 | 0.90 |
| IPI:IPI00299086.3 | SDCBP Syntenin-1 | 231.69 | | 1.00 | 0.12 | 0.60 |

TABLE 21

Increased/decreased proteins identified by Example

| Accession No. | Description | Score | Unique | Normal | IgAN | TGBM |
|---|---|---|---|---|---|---|
| IPI:IPI00640867.1 | GNAS GNAS complex locus isoform f | 231.25 | TGBM | — | — | TGBM_high |
| IPI:IPI00514055.1 | GNAS Isoform Gnas-1 of Guanine nucleotide-binding protein G(s) subunit alpha isoforms short | 231.25 | TGBM | — | — | TGBM_high |
| IPI:IPI00738905.1 | LOC648749 similar to Pancreatic alpha-amylase precursor | 231.03 | | 1.00 | — | 2.53 |
| IPI:IPI00006662.1 | APOD Apolipoprotein D precursor | 230.36 | Normal | Normal_high | — | — |
| IPI:IPI00479018.2 | SDCBP Syntenin isoform 3 | 230.17 | | 1.00 | 0.11 | 0.59 |
| IPI:IPI00021263.3 | YWHAZ 14-3-3 protein zeta/delta | 229.9 | | 1.00 | — | 0.81 |
| IPI:IPI00789337.1 | YWHAZ Tyrosine 3-monooxygenasea/tryptophan 5-monooxygenase activation protein zeta | 229.85 | | 1.00 | — | 1.07 |
| IPI:IPI00852677.1 | MUC1 isoform T11 | 229.03 | | 1.00 | 0.11 | 0.99 |
| IPI:IPI00855927.1 | MUC1 MUC1 isoform M8 | 229.03 | | 1.00 | 0.11 | 0.96 |
| IPI:IPI00335314.3 | TUBA4A Uncharacterized protein TUBA4A | 228.05 | Normal | Normal_high | — | — |
| IPI:IPI00025277.5 | PCDC6 Programmed cell death protein 6 | 227.45 | | 1.00 | — | 0.80 |
| IPI:IPI00166768.3 | TUBA1C TUBA1C protein | 226.01 | | 1.00 | — | 0.58 |
| IPI:IPI00027223.2 | IDH1 Isocitrate dehydrogenase [NADP] cytoplasmic | 225.71 | | 1.00 | — | 1.09 |

TABLE 22

Increased/decreased proteins identified by Example

| Accession No. | Description | Score | Unique | Normal | IgAN | TGBM |
|---|---|---|---|---|---|---|
| IPI:IPI00215997.5 | CD9 CD9 antigen | 224.74 | TGBM | — | — | TGBM_high |
| IPI:IPI00012113.1 | UPK2 Uroplakin-2 precursor | 224.61 | | 1.00 | — | 1.17 |
| IPI:IPI00027452.1 | SLC2A5 Solute carrier family 2, facilitated glucose transporter member 5 | 224.45 | | 1.00 | — | 1.19 |
| IPI:IPI00016513.5 | RAB10 Ras-related protein Rab-10 | 233.88 | | 1.00 | — | 0.70 |
| IPI:IPI00305551.3 | GNA11 Guanine nucleotide-binding protein subunit alpha-11 | 223.85 | | 1.00 | — | 0.99 |
| IPI:IPI00023006.1 | ACTC1 Actin, alpha cardiac muscle 1 | 223.06 | | 1.00 | 0.08 | 1.26 |
| IPI:IPI00414057.3 | ACTA1 Actin alpha 1 skeletal muscle protein | 222.53 | | 1.00 | — | 1.68 |
| IPI:IPI00017454.3 | TUBA4B Tubulin alpha-4 chain | 221.89 | Normal | Normal_high | — | — |
| IPI:IPI00219826.1 | TSG101 Isoform 2 of Tumor susceptibility gene 101 protein | 220.24 | | 1.00 | — | 0.89 |
| IPI:IPI00555900.1 | FKSG30 Kappa-actin | 219.71 | | 1.00 | — | 1.11 |
| IPI:IPI00028481.1 | RAB8A Ras-related protein Rab-8A | 219.6 | | 1.00 | — | 0.67 |
| IPI:IPI00000695.1 | GNA14 Guanine nucleotide-binding protein alpha-14 subunit | 218.41 | Normal | Normal_high | — | — |
| IPI:IPI00794699.1 | SDCBP 27 kDa protein | 218.29 | | 1.00 | 0.11 | 0.60 |
| IPI:IPI00100796.4 | CHMP5 Charged multivesicular body protein 5 | 216.38 | | 1.00 | — | 2.32 |

TABLE 23

Increased/decreased proteins identified by Example

| Accession No. | Description | Score | Unique | Normal | IgAN | TGBM |
|---|---|---|---|---|---|---|
| IPI:IPI00869052.1 | Similar to Elongation factor 1-alpha 1 | 216.09 | | 1.00 | — | 0.41 |
| IPI:IPI00021428.1 | ACTA1 Actin, alpha skeletal muscle | 214.37 | | 1.00 | 0.08 | 1.23 |
| IPI:IPI00786945.1 | LOC727848 similar to actin-like protein | 214.32 | TGBM | — | — | TGBM_high |
| IPI:IPI00871597.1 | MASP2 21 kDa protein | 209.96 | | 1.00 | — | 1.68 |
| IPI:IPI00000816.1 | YWHAE 14-3-3 protein epsilon | 208.64 | Normal | Normal_high | — | — |
| IPI:IPI00646265.1 | AMY1A; AMY1C; AMY2A; AMY1B Amylase, alpha 1B | 208.1 | | 1.00 | — | 2.56 |
| IPI:IPI00795937.1 | CD9 15 kDa protein | 207.74 | | 1.00 | — | 1.60 |
| IPI:IPI00014363.1 | BHMT2 Betaine-homocysteine S-methyltransferase 2 | 207.13 | | 1.00 | — | 1.46 |
| IPI:IPI00306378.5 | MASP2 Isoform 2 of Mannan-binding lectin serine protease 2 precursor | 207.1 | | 1.00 | — | 1.46 |
| IPI:IPI00791558.1 | HBB Delta-hemoglobin | 207.04 | | — | 1.00 | 4.53 |
| IPI:IPI00790892.1 | ENO2 6 kDa protein | 206.95 | | 1.00 | — | 0.68 |
| IPI:IPI00871366.1 | RAB1B Small GTP-binding protein | 206.62 | | 1.00 | — | 0.66 |
| IPI:IPI00006395.1 | GNAL Guanine nucleotide-binding protein G(olf) subunit alpha | 206.29 | TGBM | — | — | TGBM_high |
| IPI:IPI00032808.1 | RAB3D Ras-related protein Rab-3D | 206.09 | | 1.00 | — | 0.98 |
| IPI:IPI00073180.8 | RAB37 Ras-related protein Rab-37 | 204.67 | TGBM | — | — | TGBM_high |

TABLE 24

Increased/decreased proteins identified by Example

| Accession No. | Description | Score | Unique | Normal | IgAN | TGBM |
|---|---|---|---|---|---|---|
| IPI:IPI00025447.8 | EEF1A1 Elongation factor 1-alpha | 198.97 | | 1.00 | — | 2.53 |
| IPI:IPI00472724.1 | Elongation factor 1-alpha | 197.03 | | 1.00 | — | 4.62 |
| IPI:IPI00185072.10 | UEVLD Isoform 5 of Ubiquitin-conjugating enzyme E2 variant 3 | 195.5 | Normal | Normal_high | — | — |
| IPI:IPI00791608.1 | HSPA8 20 kDa protein | 195.26 | | 1.00 | — | 0.57 |
| IPI:IPI00748022.1 | P704P similar to actin-like protein | 195.04 | TGBM | — | — | TGBM_high |
| IPI:IPI00869004.1 | SERPINA1 Isoform 3 of Alpha-1-antitrypsin precursor | 194.98 | IgAN | — | IgAN_high | — |
| IPI:IPI00793344.1 | YWHAE 22 kDa protein | 194.66 | Normal | Normal_high | — | — |
| IPI:IPI00382804.1 | EEF1A1 EEF1A protein (Fragment) | 194.36 | | 1.00 | — | 3.60 |
| IPI:IPI00793922.1 | GAPDH 9 kDa protein | 192.47 | | 1.00 | — | 0.69 |
| IPI:IPI00410714.5 | HBA2; HBA1 Hemoglobin subunit alpha | 192.32 | | — | 1.00 | 6.62 |
| IPI:IPI00853068.1 | HBA2; HBA1 Alpha 2 globin variant (Fragment) | 192.32 | | — | 1.00 | 6.75 |
| IPI:IPI00798392.1 | RAB37 26 kDa protein | 190.35 | TGBM | — | — | TGBM_high |
| IPI:IPI00396485.3 | EEF1A1 Elongation factor 1-alpha 1 | 190.04 | | 1.00 | — | 1.23 |
| IPI:IPI00016373.3 | RAB13 Ras-related protein Rab-13 | 189.36 | | 1.00 | — | 0.73 |
| IPI:IPI00794523.2 | ACTG1; PSPHL ACTG1 protein | 188.69 | | 1.00 | 0.12 | 1.20 |

TABLE 25

Increased/decreased proteins identified by Example

| Accession No. | Description | Score | Unique | Normal | IgAN | TGBM |
|---|---|---|---|---|---|---|
| IPI:IPI00646632.3 | CNDP2 28 kDa protein | 187.84 | | 1.00 | — | 1.00 |
| IPI:IPI00022134.1 | RAB1B Putative small GTP-binding protein | 187.19 | | 1.00 | — | 0.72 |
| IPI:IPI00791421.1 | RAB37 21 kDa protein | 186.39 | TGBM | — | — | TGBM_high |
| IPI:IPI00552303.3 | ANXA11 Annexin A11 | 185.44 | | 1.00 | — | 3.53 |
| IPI:IPI00795002.1 | TUBA1C 19 kDa protein | 185.04 | | 1.00 | — | 0.76 |
| IPI:IPI00515047.2 | ACTA1 Actin, alpha 1, skeletal muscle | 184.34 | | 1.00 | 0.09 | 1.34 |
| IPI:IPI00010896.3 | CLIC1 Chloride intracellular channel protein 1 | 184.31 | | 1.00 | — | 0.84 |
| IPI:IPI00023673.1 | LGALS3BP Galectin-3-binding protein precursor | 183.02 | | 1.00 | 0.15 | 0.38 |
| IPI:IPI00413344.3 | CFL2 Cofilin-2 | 181.25 | Normal | Normal_high | — | — |
| IPI:IPI00790499.1 | RAB37 21 kDa protein | 180.41 | TGBM | — | — | TGBM_high |
| IPI:IPI00419585.9 | PPIA; PPIAL3; LOC654188 Peptidyl-prolyl cis-trans isomerase A | 179.82 | Normal | Normal_high | — | — |
| IPI:IPI00785140.2 | Uncharacterized protein ENSP00000330714 | 179.04 | | 1.00 | — | 0.92 |
| IPI:IPI00180730.1 | Elongation factor 1-alpha | 178.55 | Normal | Normal_high | — | — |
| IPI:IPI00329441.1 | ISY1; RAB43 Ras-related protein Rab-43 | 177.34 | | 1.00 | — | 0.90 |

TABLE 26

Increased/decreased proteins identified by Example

| Accession No. | Description | Score | Unique | Normal | IgAN | TGBM |
|---|---|---|---|---|---|---|
| IPI:IPI00736860.2 | ELK2, member of ETS oncogene family, pseudogene 1 | 177.21 | | 1.00 | 2.86 | 2.46 |
| IPI:IPI00645370.1 | VPS4B 16 kDa protein | 177.1 | | 1.00 | 0.13 | 0.88 |
| IPI:IPI00002926.4 | VPS37B Vacuolar protein sorting-associated protein 37B | 176.93 | | 1.00 | — | 1.08 |
| IPI:IPI00477489.1 | RAB4B Isoform 1 of Ras-related protein Rab-4B | 176.87 | TGBM | — | — | TGBM_high |
| IPI:IPI00012540.1 | PROM1 Prominin-1 precursor | 176.63 | | 1.00 | 0.19 | 0.99 |
| IPI:IPI00745705.2 | LOC730924 similar to Pancreatic alpha-amylase precursor | 175.5 | | 1.00 | — | 2.46 |
| IPI:IPI00788782.1 | ATP1A3 Cation-transporting ATPase | 175.36 | | 1.00 | 1.09 | — |
| IPI:IPI00302840.2 | ATP1A3 Sodium/potassium-transporting ATPase subunit alpha-3 | 175.36 | | 1.00 | 0.03 | — |
| IPI:IPI00430842.3 | IGHA1 IGHA1 protein | 175.11 | | 1.00 | 0.97 | 1.45 |
| IPI:IPI00798247.1 | HSPA8 20 kDa protein | 174.84 | | 1.00 | — | 1.45 |
| IPI:IPI00060801.1 | RAB39B Ras-related protein Rab-39B | 173.59 | TGBM | — | — | TGBM_high |
| IPI:IPI00014424.1 | EEF1A2 Elongation factor 1-alpha 2 | 172.45 | | 1.00 | — | 4.10 |
| IPI:IPI00844239.1 | Immunoblobulin G1 Fab heavy chain variable region (Fragment) | 172.25 | | — | 1.00 | 1.05 |
| IPI:IPI00218918.5 | ANXA1 Annexin A1 | 170.07 | Normal | Normal_high | — | — |

TABLE 27

Increased/decreased proteins identified by Example

| Accession No. | Description | Score | Unique | Normal | IgAN | TGBM |
|---|---|---|---|---|---|---|
| IPI:IPI00246975.8 | GSTM3 Glutathione S-transferase Mu 3 | 160.98 | Normal | Normal_high | — | — |
| IPI:IPI00015148.3 | RAP1B Ras-related protein Rap-1b precursor | 159.81 | | 1.00 | 0.36 | 1.32 |
| IPI:IPI00845493.1 | Brain type mu-glutathione S-transferase | 159.72 | Normal | Normal_high | — | — |
| IPI:IPI00872974.1 | GSTA2 Glutathione S-transferase | 158.01 | | 1.00 | — | 0.77 |
| IPI:IPI00169383.3 | PGK1 Phosphoglycerate kinase 1 | 157.34 | | 1.00 | — | 0.55 |
| IPI:IPI00005719.1 | RAB1A Isoform 1 of Ras-related protein Rab-1A | 156.04 | | 1.00 | — | 0.70 |
| IPI:IPI00787396.1 | GNAT3 similar to Guanine nucleotide-binding protein G(t), alpha-3 subunit | 154.41 | TGBM | — | — | TGBM_high |
| IPI:IPI00797556.1 | ANXA2 24 kDa protein | 153.1 | Normal | Normal_high | — | — |
| IPI:IPI00019345.1 | RAP1A Ras-related protein Rap-1A precursor | 152.92 | | 1.00 | 0.36 | 1.35 |
| IPI:IPI00796467.1 | TF 11 kDa protein | 152.91 | | — | 1.00 | 0.44 |
| IPI:IPI00023510.1 | RAB5A Ras-related protein Rab-5A | 152.53 | TGBM | — | — | TGBM_high |
| IPI:IPI00657682.2 | GSTA1 Glutathione S-transferase A1 | 151.68 | | 1.00 | — | 0.71 |
| IPI:IPI00783387.1 | Immunglobulin heavy chain variable region (Fragment) | 150.22 | | 1.00 | 1.06 | — |

TABLE 28

Increased/decreased proteins identified by Example

| Accession No. | Description | Score | Unique | Normal | IgAN | TGBM |
|---|---|---|---|---|---|---|
| IPI:IPI00022977.1 | CKB Creatine kinase B-type | 407.27 | | 1.00 | — | 0.73 |
| IPI:IPI00219018.7 | GAPDH Glyceraldehyde-3-phosphate dehydrogenase | 407.22 | | 1.00 | — | 0.84 |
| IPI:IPI00472610.2 | IGHM IGHM protein | 406.9 | | 1.00 | 5.26 | 4.85 |
| IPI:IPI00411356.5 | VPS4A Vacuolar protein sorting-associating protein 4A | 406.68 | | 1.00 | — | 0.83 |
| IPI:IPI00440160.2 | UEVLD Isoform 3 of Ubiquitin-conjugating enzyme E2 variant 3 | 406.44 | | 1.00 | — | 1.00 |
| IPI:IPI00154742.6 | IGL@ IGL@ protein | 406.41 | IgAN | — | IgAN_high | — |
| IPI:IPI00021447.1 | AMY2B Alpha-amylase 2B precursor | 405.88 | | 1.00 | — | 3.71 |
| IPI:IPI00784519.1 | Putative uncharacterized protein | 405.02 | IgAN | — | IgAN_high | — |
| IPI:IPI00450309.1 | IGL@ IGL@ protein | 404.64 | IgAN | — | IgAN_high | — |
| IPI:IPI00796167.1 | IGL@ IGL@ protein | 404.12 | IgAN | — | IgAN_high | — |
| IPI:IPI00217269.3 | GNAT2 Guanine nucleotide-binding protein G(t) subunit alpha-2 | 403.37 | | 1.00 | — | 1.13 |
| IPI:IPI00032328.2 | KNG1 Isoform HMW of Kininogen-1 precursor | 401.91 | | 1.00 | — | 0.78 |
| IPI:IPI00003348.3 | GNB2 Guanine nucleotide-binding protein G(I)/G(S)/G(T) subunit beta-2 | 398.88 | | 1.00 | — | 1.17 |
| IPI:IPI00000885.1 | FRK Tyrosine-protein kinase FRK | 398.32 | | 1.00 | — | 0.73 |
| IPI:IPI00785196.1 | Putative uncharacterized protein | 398.06 | IgAN | — | IgAN_high | — |

TABLE 29

Increased/decreased proteins identified by Example

| Accession No. | Description | Score | Unique | Normal | IgAN | TGBM |
|---|---|---|---|---|---|---|
| IPI:IPI00657796.1 | CD9 Uncharacterized protein CD9 | 204.5 | | 1.00 | — | 1.90 |
| IPI:IPI00063827.1 | ABHD14B Isoform 1 of Abhydrolase domain-containing protein 14B | 204.45 | | 1.00 | — | 0.73 |
| IPI:IPI00644936.1 | GNAS Isoform 3 of Guanine nucleotide-binding protein G(s) subunit alpha isoforms short | 204.01 | TGBM | — | — | TGBM_high |
| IPI:IPI00024282.1 | RAB8B Ras-related protein Rab-8B | 203.65 | | 1.00 | — | 0.69 |
| IPI:IPI00514530.4 | ACTA1 Uncharacterized protein ACTA1 | 202.61 | | 1.00 | 0.09 | 1.25 |
| IPI:IPI00480056.7 | RAB4A Uncharacterized protein RAB4A | 202.54 | | 1.00 | — | 1.07 |
| IPI:IPI00103065.4 | MITD1 MIT domain-containing protein 1 | 201.63 | Normal | Normal_high | — | — |
| IPI:IPI00061114.1 | RAB3C Ras-related protein Rab-3C | 200.34 | | 1.00 | — | 0.91 |
| IPI:IPI00871276.1 | RAB3C 26 kDa protein | 200.34 | | 1.00 | — | 0.90 |
| IPI:IPI00219835.1 | GNAS Isoform Gnas-2 of Guanine nucleotide-binding protein G(s) subunit alpha isoforms short | 200.12 | TGBM | — | — | TGBM_high |

TABLE 29-continued

Increased/decreased proteins identified by Example

| Accession No. | Description | Score | Unique | Normal | IgAN | TGBM |
|---|---|---|---|---|---|---|
| IPI:IPI00641459.3 | EEF1A1 Similar to Elongation factor 1 alpha | 199.31 | | 1.00 | — | 0.43 |
| IPI:IPI00377081.1 | STOM stomatin isoform b | 199.14 | | 1.00 | — | 0.68 |

TABLE 30

Increased/decreased proteins identified by Example

| Accession No. | Description | Score | Unique | Normal | IgAN | TGBM |
|---|---|---|---|---|---|---|
| IPI:IPI00745660.2 | IGL@ IGL@ protein | 302.18 | IgAN | — | IgAN_high | — |
| IPI:IPI00294713.4 | MASP2 Isoform 1 of Mannan-binding lectin serine protease 2 precursor | 300.93 | | 1.00 | — | 1.49 |
| IPI:IPI00022255.1 | OLFM4 Olfactomedin-4 precursor | 300.3 | | 1.00 | 0.07 | 1.86 |
| IPI:IPI00784627.1 | Putative Uncharacterized protein | 300.12 | IgAN | — | IgAN_high | — |
| IPI:IPI00784713.1 | Putative Uncharacterized protein | 300.12 | IgAN | — | IgAN_high | — |
| IPI:IPI00871793.1 | MASP2 77 kDa protein | 299.96 | | 1.00 | — | 2.69 |
| IPI:IPI00790490.1 | GPRC5C 48 kDa protein | 295.74 | | 1.00 | 0.12 | 1.39 |
| IPI:IPI00099883.4 | GPRC5C G-protein coupled receptor family C group 5 member C precursor | 295.74 | | 1.00 | 0.12 | 1.36 |
| IPI:IPI00291262.3 | CLU Clusterin precursor | 295.66 | TGBM | — | — | TGBM_high |
| IPI:IPI00795633.1 | CLU CLU | 295.66 | TGBM | — | — | TGBM_high |
| IPI:IPI00789107.1 | RPS27A; UBC; UBB 30 kDa protein | 294.28 | | 1.00 | 0.19 | 0.83 |
| IPI:IPI00784983.1 | Putative Uncharacterized protein | 293.91 | IgAN | — | IgAN_high | — |
| IPI:IPI00026268.3 | GNB1 Guanine nucleotide-binding protein G(I)/G(S)/G(T) subunit beta-1 | 292.14 | | 1.00 | — | 1.14 |
| IPI:IPI00791613.1 | TUBA8 52 kDa protein | 291.34 | Normal | Normal_high | — | — |

TABLE 31

Increased/decreased proteins identified by Example

| Accession No. | Description | Score | Unique | Normal | IgAN | TGBM |
|---|---|---|---|---|---|---|
| IPI:IPI00465380.6 | GNAS Uncharacterized protein GNAS (Fragment) | 168.01 | | 1.00 | — | 0.69 |
| IPI:IPI00797951.1 | HSPA8 16 kDa protein | 166.78 | | 1.00 | — | 1.43 |
| IPI:IPI00788210.1 | LOC728590 similar to ribosomal protein S27a | 166.62 | | 1.00 | — | 0.59 |
| IPI:IPI00792992.1 | RAB37 22 kDa protein | 166.16 | TGBM | — | — | TGBM_high |
| IPI:IPI00550181.2 | CHMP2B Charged multivesicular body protein 2b | 166.07 | | 1.00 | — | 1.28 |
| IPI:IPI00023504.1 | RAB3A Ras-related protein Rab-3A | 165.51 | TGBM | — | — | TGBM_high |
| IPI:IPI00556414.1 | Mel transforming oncogene variant (Fragment) | 165.16 | | 1.00 | — | 0.75 |

TABLE 31-continued

Increased/decreased proteins identified by Example

| Accession No. | Description | Score | Unique | Normal | IgAN | TGBM |
|---|---|---|---|---|---|---|
| IPI:IPI00412525.1 | hCG_1757335; RAP1B Uncharacterized protein ENSP00000345280 | 164.4 | | 1.00 | 0.41 | 1.28 |
| IPI:IPI00220301.5 | PRDX6 Peroxiredoxin-6 | 163.55 | | 1.00 | — | 0.58 |
| IPI:IPI00477090.6 | IGHM IGHM protein | 163.16 | IgAN | — | IgAN_high | — |
| IPI:IPI00873902.1 | RAB1A 23 kDa protein | 162.44 | | 1.00 | — | 0.67 |
| IPI:IPI00187143.1 | RAB4B Isoform 2 of Ras-related protein Rab-4B | 162.37 | TGBM | — | — | TGBM_high |
| IPI:IPI00854833.1 | RAP1A Uncharacterized protein RAP1A | 161.39 | | 1.00 | — | 1.63 |

TABLE 32

Increased/decreased proteins identified by Example

| Accession No. | Description | Score | Unique | Normal | IgAN | TGBM |
|---|---|---|---|---|---|---|
| IPI:IPI00797482.1 | RPS27A; UBC; UBB CDNA FLJ32377 fis, clone SKMUS1000014, highly similar to Polyubiquitin 9 | 386.38 | | 1.00 | 0.19 | 0.83 |
| IPI:IPI00788737.1 | GAPDH 39 kDa protein | 384.98 | | 1.00 | — | 0.89 |
| IPI:IPI00643007.1 | KIAA0174 Isoform 3 of Uncharacterized protein KIAA0174 | 383.66 | | 1.00 | 0.17 | 1.67 |
| IPI:IPI00797523.1 | HSPA8 20 kDa protein | 383.66 | | 1.00 | — | 0.71 |
| IPI:IPI00397808.3 | LOC388720 similar to ubiquitin and ribosomal protein S27a precursor | 382.66 | | 1.00 | — | 0.81 |
| IPI:IPI00215894.1 | KNG1 Isoform LMW of Kininogen-1 precursor | 382.13 | | 1.00 | — | 0.81 |
| IPI:IPI00797833.3 | KNG1 Kininogen 1 | 382.13 | | 1.00 | — | 0.78 |
| IPI:IPI00796633.1 | TPI1 22 kDa protein | 381.1 | | 1.00 | — | 0.94 |
| IPI:IPI00016339.4 | RAB5C Ras-related protein Rab-5C | 380.62 | | 1.00 | — | 1.12 |
| IPI:IPI00017160.3 | VTA1 Vacuolar protein sorting-associated protein VTA1 homolog | 378.92 | | 1.00 | — | 0.79 |
| IPI:IPI00642632.1 | C7 protein | 376.2 | IgAN | — | IgAN_high | — |
| IPI:IPI00300786.1 | AMY1A; AMY1C; AMY2A; AMY1B Alpha-amylase 1 precursor | 375.66 | | 1.00 | — | 2.80 |
| IPI:IPI00793930.1 | TUBA1B TUBA1B protein | 375.65 | | 1.00 | — | 1.01 |
| IPI:IPI00816314.1 | IGHM Putative uncharacterized protein DKFZp686I15196 | 375.23 | | 1.00 | 5.00 | 4.66 |
| IPI:IPI00018901.2 | GGT1 Isoform 1 of Gamma-glutamyltranspeptidase 1 precursor | 369.2 | | 1.00 | — | 0.62 |

TABLE 33

Increased/decreased proteins identified by Example

| Accession No. | Description | Score | Unique | Normal | IgAN | TGBM |
|---|---|---|---|---|---|---|
| IPI:IPI00396108.2 | GPRC5C G protein-coupled receptor family C, group 5, member C isoform a | 321.89 | | 1.00 | 0.11 | 1.39 |

TABLE 33-continued

Increased/decreased proteins identified by Example

| Accession No. | Description | Score | Unique | Normal | IgAN | TGBM |
|---|---|---|---|---|---|---|
| IPI:IPI00785164.1 | Putative Uncharacterized protein | 321.63 | IgAN | — | IgAN_high | — |
| IPI:IPI00788054.1 | GGT2 similar to Gamma-glutamyltranspeptidase 1 precursor (Gamma-glutamyltransferase 1) (CD224 antigen) isoform 2 | 321.37 | | 1.00 | — | 0.58 |
| IPI:IPI00607626.1 | FLOT1 Flotillin 1 | 321.32 | Normal | Normal_high | — | — |
| IPI:IPI00785084.1 | Immunoglobulin heavy variable 4-31 | 321.29 | | — | 1.00 | 0.91 |
| IPI: IPI00301277.1 | HSPA1L Heat shock 70 kDa protein 1L | 319.05 | | 1.00 | — | 1.36 |
| IPI: IPI00643152.1 | HSPA1L Heat shock 70 kDa protein 1-like variant | 319.05 | | 1.00 | — | 1.20 |
| IPI:IPI00218488.3 | GNAT1 Guanine nucleotide-binding protein G(t) subunit alpha-1 | 318.67 | | 1.00 | — | 1.13 |
| IPI:IPI00815938.1 | IGLV3-21 IGLV3-21 protein | 316.8 | IgAN | — | IgAN_high | — |
| IPI:IPI00745360.1 | GGT2 Uncharacterized protein ENSP00000255845 | 316.54 | | 1.00 | — | 0.64 |
| IPI:IPI00829711.1 | IGHA2 Uncharacterized protein IGHA2 (Fragment) | 314.86 | | 1.00 | 0.84 | 1.13 |
| IPI:IPI00793729.1 | RPS27A; UBC; UBB UBC protein | 314.72 | | 1.00 | 0.19 | 0.82 |
| IPI:IPI00248911.7 | GNAT3 guanine nucleotide binding protein, alpha transducing 3 | 313.56 | | 1.00 | — | 1.12 |
| IPI:IPI00004901.5 | GPRC5C CDNA FLJ20242 fis, clone COLF6369 | 313.55 | | 1.00 | 0.14 | 1.32 |

Figure 3:
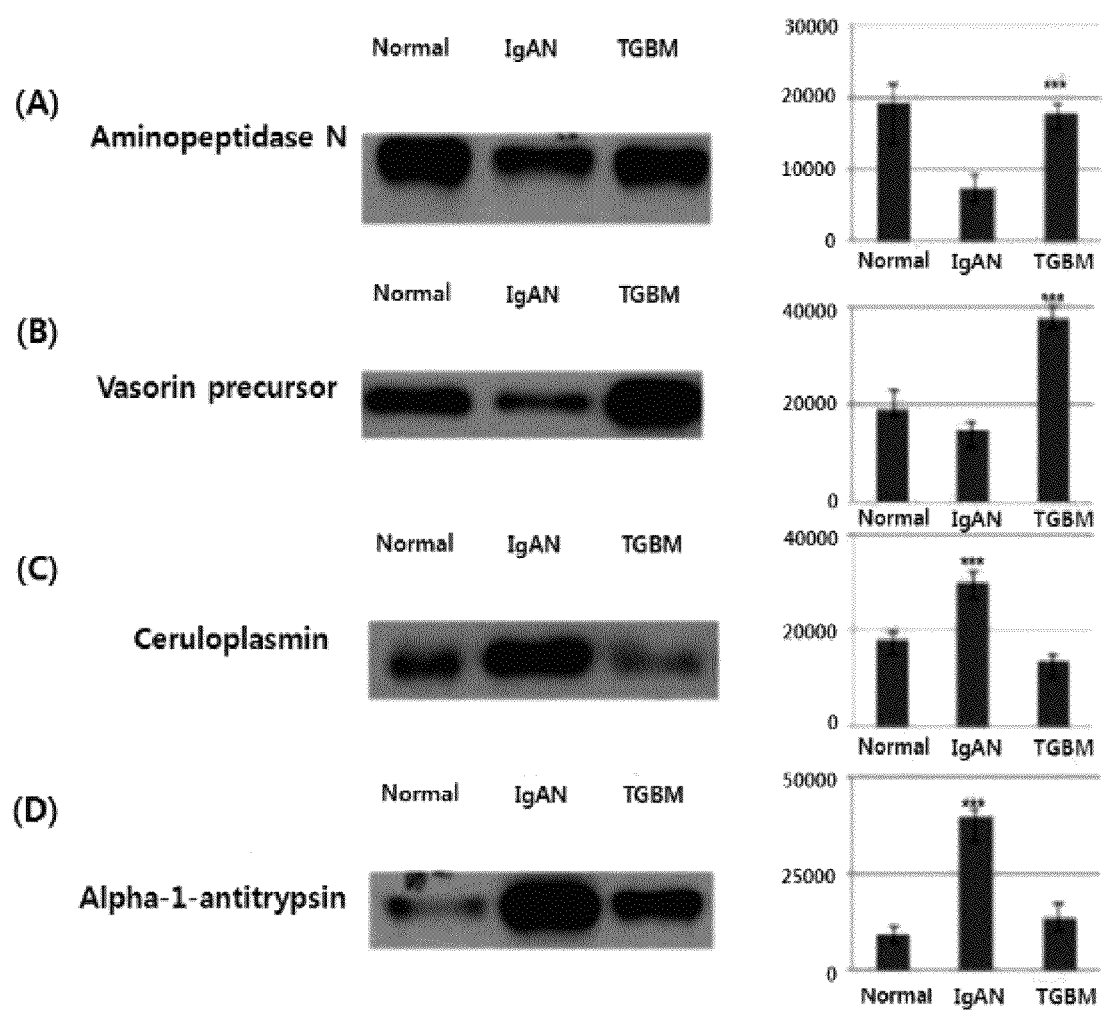
FIG. 3 shows western blot photographs of proteins according to the present invention that who increased/decreased levels in patients.

In the present invention, from among proteins increased/decreased in IgA nephropathy patients and TGBM nephropathy patients, Aminopeptidase N, Vasorin precursor, Ceruloplasmin, and Alpha-1-antitrypsin were selected and subjected to western blot. The result is shown in FIG. 3 (Normal: normal people, IgAN: IgA nephropathy patients, TGBM: TGBM nephropathy patients).

INDUSTRIAL APPLICABILITY

Although several exemplary embodiments of the present invention have been described for illustrative purposes, those skilled in the art will appreciate that various modifications, additions and substitutions are possible, without departing from the scope and spirit of the invention as disclosed in the accompanying claims.

The invention claimed is:

1. A method of detecting IgA nephropathy in a patient suspected of having IgA nephropathy using urine exosome from said patient comprising:
   obtaining a urine sample from said patient;
   separating exosome from said urine sample;
   performing an immunoassay on said urine exosome comprising reacting said urine exosome with isolated monoclonal or polyclonal antibodies specifically binding to at least three different proteins selected from the group consisting of Ceruloplasmin precursor having Accession No. IPI00017601.1, Alpha-1-antitrypsin precursor having Accession No. IPI00553177.1, Serotransferrin precursor having Accession No. IPI00022463.1, Transferrin variant Fragment having Accession No. IPI00798430.1, and Alpha-2-macroglobulin precursor having Accession No. IPI00478003.1 to obtain at least three different specifically bound antibody-protein complexes;
   measuring levels of said at least three different specifically bound antibody-protein complexes to determine expression levels of said at least three different proteins in said urine exosome;
   detecting whether said urine exosome contains increased levels of said at least three different proteins by comparing said expression levels of said at least three different proteins in said urine exosome to levels of said at least three different proteins in urine exosome samples from healthy patients; and
   diagnosing that said patient has IgA nephropathy if said patient's urine exosome contains significantly higher levels of said at least three different proteins compared to said levels of said at least three different proteins in urine exosome samples from healthy patients.

2. The method of claim 1, wherein said isolated monoclonal or polyclonal antibodies are said anti-Ceruloplasmin, said anti-Transferrin variant Fragment, and said anti-Alpha-2-macroglobulin precursor.

* * * * *